United States Patent
Liu et al.

(10) Patent No.: US 12,076,338 B1
(45) Date of Patent: *Sep. 3, 2024

(54) DEVICES FOR TREATING DISEASES AND CONDITIONS

(71) Applicant: Tesla BioHealing Inc., Milford, DE (US)

(72) Inventors: James Zhou Liu, Milford, DE (US); Yuehua Gu, Monmouth Junction, NJ (US)

(73) Assignee: Tesla BioHealing Inc., Milford, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/598,402

(22) Filed: Mar. 7, 2024

Related U.S. Application Data

(60) Provisional application No. 63/562,387, filed on Mar. 7, 2024, provisional application No. 63/548,967, filed on Feb. 2, 2024.

(51) Int. Cl.
| | | |
|---|---|---|
| *A61K 33/00* | (2006.01) | |
| *A61K 47/38* | (2006.01) | |
| *A61P 9/10* | (2006.01) | |

(52) U.S. Cl.
CPC .............. *A61K 33/00* (2013.01); *A61K 47/38* (2013.01)

(58) Field of Classification Search
CPC ........ A61K 33/00; A61K 33/06; A61K 33/26; A61K 33/34; A61K 47/38; A61B 2018/0046; A61P 9/10

See application file for complete search history.

(56) References Cited

U.S. PATENT DOCUMENTS

| | | |
|---|---|---|
| 2003/0181949 A1 | 9/2003 | Whale |
| 2005/0170979 A1 | 8/2005 | Massaro |
| 2020/0102484 A1 | 4/2020 | Gutsulyak |

FOREIGN PATENT DOCUMENTS

| | | | |
|---|---|---|---|
| KR | 20110095602 A | 8/2011 | |
| WO | WO-2007118430 A1 * | 10/2007 | .......... A61K 31/165 |

OTHER PUBLICATIONS

Salehpour et al. Photobiomodulation, Photomedicine, and Laser Surgery vol. 37, No. 10, 2019: pp. 581-595. (Year: 2019).*
English translation WO2007118430; 2007:30 pages. (Year: 2007).*
Zhongin Zu Chapter 1 in: Fundamentals of Air Cleaning Technology and Its Application in Cleanrooms. Aug. 7, 2013 : 1-46. (Year: 2013).*
Biophoton (https://en.wikipedia.org/wiki/Biophoton), downloaded Aug. 9, 2023.
Bioplasm 9D-NLS Bioresonance Machine - Aura Chakra Healing, available at https://www.biophiliatracker.com/Bioplasm-9D, downloaded May 24, 2023.
Complete Neurologic Exam, p1-3, downloaded Jan. 29, 2024.

(Continued)

*Primary Examiner* — Ernst V Arnold
(74) *Attorney, Agent, or Firm* — Greenberg Traurig, LLP

(57) ABSTRACT

Disclosed herein are medical devices, uses thereof, methods of manufacture, and kits comprising medical devices. Also disclosed herein are uses of medical devices. For example, medical devices are used to produced biophotons for biophoton therapy. Also disclosed herein is the administration of biophoton therapy for the treatment of stroke in a subject in need thereof.

20 Claims, 7 Drawing Sheets

(56) References Cited

OTHER PUBLICATIONS

Hamblin, Do Biophotons Play Any Role in Transcranial Photobiomodulation of the Brain?, Photobiomodulation, Photomedicine, and Laser Surgery, 2022, vol. 40, No. 11, p731-733.
Hamblin, Shining light on the head: Photobiomodulation for brain disorders, BBA Clinical, 2016, vol. 6, p. 113-124.
Mat, Amethyst, Properties, Formation, Occurrences, Geology Science, modified Apr. 23, 2023, https://geologyscience.com/minerals/amethyst/, downloaded Sep. 27, 2023.
Mat, Obsidian, Properties, Formation, Occurrences and Uses Thereof, Geology Science, modified Sep. 9, 2023, https://geologyscience.com/minerals/obsidian/, downloaded Sep. 27, 2023.
Mat, Tourmaline, Properties, Formation, Occurrences, Geology Science, modified Aug. 6, 2023, https://geologyscience.com/minerals/tourmaline/, downloaded Sep. 27, 2023.
Moro et al., The code of light: do neuronsgenerate light to communicate and repair?, Neural Regeneration Research, 2022, vol. 17, No. 6, p. 1251-1252.
Moro et al., The effect of photobiomodulation on the brain during wakefulness and sleep; Frontiers in Neuroscience; 2022; p. 1-15.
NIH. (https://newsinhealth.nih.gov/2013/04/benefits-slumber).
Oros, Biophoton Emission From Plants: a Contribution To the Understanding of Plant Signaling, Naval Postgraduate School, 2018, p. 1-13.
Salieres, Measurements of the level of biophoton emission of wines from different viti-vinicultural practices, EnerLab, 2021, p. 1-23.
SF-36 Questionnaire, p. 1-5, downloaded Jan. 29, 2024.
Stroke Impact Scale, Questionnaire, p. 1-9, downloaded Jan. 29, 2024.
Tang et al., Biophoton signal transmission and processing in the brain, Journal of Photochemistry and Photobiology B: Biology, Science Direct, 2014, p. 1-5.
Thorlabs, https://www.thorlabs.com/newgrouppage9.cfm?objectgroup_id=15805, downloaded Mar. 5, 2024.
WebMD (WebMD: https://www.webmd.com/sleep-disorders/benefits-sleep-more#1), downloaded May 24, 2023.

* cited by examiner

Biophotons Detected from two Different Water Bottles

Water before Energized

Water after Energized

DEVICES FOR TREATING DISEASES AND CONDITIONS

CROSS REFERENCE TO RELATED APPLICATION

This application claims priority to U.S. Provisional Application No. 63/562,387, filed on Mar. 7, 2024 and U.S. Provisional Application No. 63/548,967, filed on Feb. 2, 2024, the disclosures of which are incorporated herein by reference in their entirety.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY

Disclosed herein are medical devices. In some embodiments, a medical device can comprise a substantially heterogeneous mixture of: (a) a stone selected from the group consisting of: a diamond, an amethyst, a tourmaline, a jade, an obsidian, and any combination thereof; (b) a sand comprising at least about 95% silicon dioxide by weight; (c) a metal selected from the group consisting of: a copper, an iron, and any combination thereof; (d) a polymer selected from the group consisting of: an isoprene rubber, a butyl rubber, a cellulose, a polysaccharide, or any combination thereof; (e) a water; and (d) a supporting material selected from the group consisting of: a grout, a modified sulfur cement, an agar, and any combination thereof. In some embodiments, the stone, the sand, the metal, and the polymer can comprise particles that each comprise a particle size diameter ranging from about 0.1 mm to about 5 mm. In some embodiments, the medical device can comprise biophotons as measured by a biophoton detector. In some embodiments, the weight to weight ratio of the stone, the sand, the metal, the polymer, and the water can be equal. In some embodiments, the weight to weight ratio of the stone, the sand, the metal, the polymer, the water and the supporting material can be about 10% the stone: 10% the sand: 10% the metal: 50% the polymer: 10% the water: and about 10% the supporting material. In some embodiments, the stone can be the diamond. In some embodiments, the stone can be the amethyst. In some embodiments, the stone can be the tourmaline. In some embodiments, the stone can be the jade. In some embodiments, the stone can be the obsidian. In some embodiments, the metal can be the copper. In some embodiments, the metal can be the iron. In some embodiments, the polymer can be the isoprene rubber. In some embodiments, the polymer can be the butyl rubber. In some embodiments, the polymer can be the cellulose. In some embodiments, the cellulose can comprise an alpha cellulose or a salt thereof. In some embodiments, the polymer can be the polysaccharide. In some embodiments, the polysaccharide can comprise a hyaluronic acid or a salt thereof. In some embodiments, the supporting material can be the grout. In some embodiments, the supporting material can be the modified sulfur cement. In some embodiments, the supporting material can be the agar.

Also disclosed herein are methods comprising placing the medical device disclosed herein within about 0.1 meters to about 10 meters from a biological system for at least 15 minutes. In some embodiments, the biological system can be a human, an animal, a microbial culture, or a plant.

Also disclosed herein are methods of treating a stroke in a subject in need thereof. In some embodiments, a method can comprise placing a medical device disclosed herein within about 0.1 meters to about 5 meters from a subject for at least about 1 hour per day. In some embodiments, the medical device can be placed within about 0.1 meters to about 5 meters from the subject for at least about 8 hours per day. In some embodiments, the subject can have an increase in their Stroke Impact Scale (SIS) score after about 1 week of treatment as compared to a subject who was not within about 0.1 meters to about 5 meters from a medical device for at least about 1 hour per day. In some embodiments, the subject can have an increase in their SF-36 score after about 1 week of treatment as compared to a subject who was not within about 0.1 meters to about 5 meters from a medical device for at least about 1 hour per day. In some embodiments, the subject can have an increase in their stroke recovery rate score after about 1 week of treatment as compared to a subject who was not within about 0.1 meters to about 5 meters from a medical device for at least about 1 hour per day. In some embodiments, the subject can have an increase in their neurological exam score after about 1 week of treatment as compared to a subject who was not within about 0.1 meters to about 5 meters from a medical device for at least about 1 hour per day.

Also disclosed herein are methods of treating a disease or condition in need thereof. In some embodiments, the method can comprise placing the medical device disclosed herein within about 0.1 meters to about 5 meters from a subject for at least about 1 hour per day. In some embodiments, the medical device can be placed within about 0.1 meters to about 5 meters from the subject for at least about 8 hours per day. In some embodiments, the disease or condition can be selected from: an Alzheimer's disease, a Parkinson's disease, a Traumatic Brain Injury (TBI), a depression, a stroke, an epilepsy, a cancer, an anemia, a long COVID-19, an asthma, a Chronic Obstructive Pulmonary Disease (COPD), a glaucoma, a mitochondrial deficiency, a diabetes, a hypertension, an insomnia, a chronic pain, an acute pain, a neuromuscular disease, a kidney disease, and any combination thereof.

BRIEF DESCRIPTION OF THE DRAWINGS

The features of the disclosure are set forth with particularity in the appended claims. A better understanding of the features and advantages of the present disclosure can be obtained by reference to the following detailed description that sets forth illustrative embodiments, in which the principles of the disclosure are utilized, and the accompanying drawings of which:

FIG. 1A shows the biophoton release from Device A and FIG. 1B shows the biophoton release from Device B released as measured by a MIRA camera. The Y-axis of the figures indicates the amount of biophotons released, the X-axis shows the captured image frame of the recording by the camera over time.

DETAILED DESCRIPTION

Overview

Figure 1A:
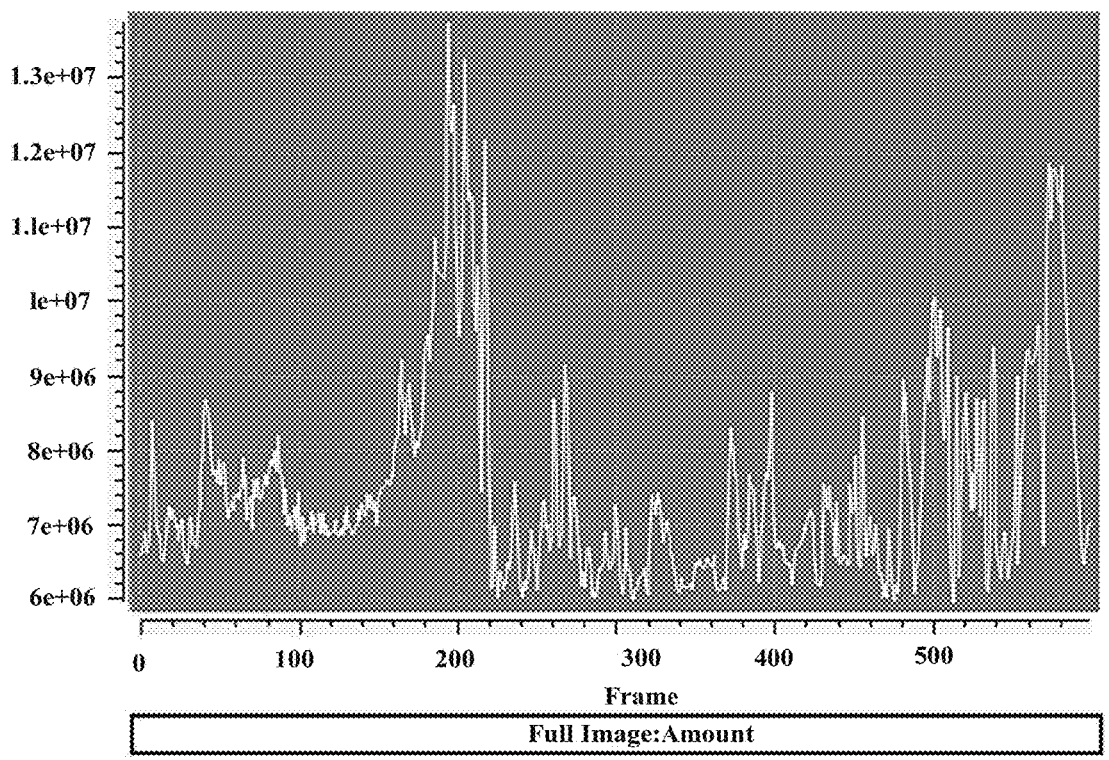
FIGS. 1A-1B shows biophoton release from two different medical devices.

The current disclosure provides biophoton therapies to restore cellular activities, to slow down aging, and to treat diseases and conditions, such as a stroke, a traumatic brain injury, an Alzheimer's Disease, a dementia, a Parkinson's Disease, a chronic obstructive pulmonary disease (COPD), an asthma, a genetic mutation, a cancer, a chronic pain, or other diseases disclosed herein. Biophoton therapies disclosed herein can be produced by a medical device. A medical device comprises different materials that when combined produce biophotons. Also disclosed herein are kits comprising a medical device and methods for manufacturing the medical device. A medical device can be placed near a subject and be used to produce biophotons for biophoton therapy of a subject. The biophotons emitted by the medical device can be used to modulate biological processes and restore cellular function.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various aspects may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, the term 'about' a number can refer to that number plus or minus 10% of that number. The term 'about' a range can refer to that range minus 10% of its lowest value and plus 10% of its greatest value.

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing," "assaying," and "analyzing" are often used interchangeably herein to refer to forms of measurement and include determining if an element may be present or not (for example, detection). These terms may include quantitative and/or qualitative determinations. Assessing may be alternatively relative or absolute. "Detecting the presence of" includes determining the amount of something present, as well as determining whether it may be present or absent.

The terms "subject," "individual," or "patient" are often used interchangeably herein. A "subject" may be a biological entity. The biological entity may be a plant, animal, or microorganism, including, for example, bacteria, viruses, fungi, and protozoa. The subject may be tissues, cells and their progeny of a biological entity obtained in vivo or cultured in vitro. The subject may be a mammal. The mammal may be a human. The subject may be diagnosed or suspected of being at high risk for a disease. In some cases, the subject may not be necessarily diagnosed or suspected of being at high risk for the disease. In some cases, the subject may be healthy (e.g., the subject may not have a significant disease). In some cases, a subject can be a child or an adult. In some cases, a subject can be about 1 day of age to about 18 years of age, 1 day of age to about 120 years of age, 18 years of age to about 120 years of age, or 60 years of age to about 120 years of age.

The term "at least partially" may refer to a qualitative condition that exhibits a partial range or degree of a feature or characteristic of interest. For example, at least partially can comprise a partial range or degree of a feature or characteristic of interest that is at least about: 5%, 10%, 20%, 30%, 40%, 50%, 60%, 70%, 75%, 80%, 85%, 90%, 95%, 99%, or 100% of the feature or characteristic.

The term "in vivo" may be used to describe an event that takes place in a subject's body. The term "ex vivo" may be used to describe an event that takes place outside of a subject's body. An "ex vivo" assay may not be performed on a subject. Rather, it may be performed upon a sample separate from a subject. An example of an "ex vivo" assay performed on a sample may be an "in vitro" assay.

The term "in vitro" may be used to describe an event that takes place contained in a container for holding laboratory reagent such that it may be separated from the living biological source organism from which the material may be obtained. In vitro assays may encompass cell-based assays in which cells alive or dead are employed. In vitro assays may also encompass a cell-free assay in which no intact cells are employed.

As used herein, the terms "treatment" or "treating" are used in reference to a pharmaceutical or other intervention regimen (e.g., a biophoton therapy) for obtaining beneficial or desired results in the recipient such as reducing the symptoms of a stroke in a subject. Beneficial or desired results include but are not limited to a therapeutic benefit and/or a prophylactic benefit. Beneficial or desired results include but are not limited to treatment of a complication of a disease. A therapeutic benefit may refer to eradication or amelioration of symptoms or of an underlying disorder being treated. Also, a therapeutic benefit may be achieved with the eradication or amelioration of one or more of the physiological symptoms associated with the underlying disorder such that an improvement may be observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For a prophylactic benefit, a subject at risk of developing a particular disease, or to a subject reporting one or more of the physiological symptoms of a disease may undergo treatment, even though a diagnosis of this disease may not have been made.

Without being bound to any theories, biophotons can be light-based particles that can have dual particle/wave properties and can be used to treat a disease or condition of a subject or supplement the health of a subject. Without being bound to any theories, biophotons can comprise a quantum particle. In some embodiments, a biophoton can comprise a photon. Without being bound to any theories, a biophoton can comprise a photon of light in the ultraviolet and low visible light range that are produced by a system disclosed herein. In some cases, a biophoton can radiant emittance in the visible and ultraviolet frequencies ranges from $10^{17}$ to $10^{23}$ W/cm$^2$. In some cases, a biophoton herein can be in the wavelength range of about 200 nanometers (nm) to about 800 nm. In some cases, a biophoton herein can be in the wavelength range of about 200 and 1300 nanometers. Without being bound to any theories, a biophoton can comprise an infrared radiation. In some cases, infrared radiation can be electromagnetic radiation with wavelengths between 760 nm and 100,000 nm. Without being bound to any theories, a biophoton can comprise a low-level light therapy (LLLT) or photobiomodulation (PBM). In some cases, low-level light therapy (LLLT) or photobiomodulation (PBM) can comprise light at red and near-infrared wavelengths (600-1000 nm). In some cases, far infrared light can be comprised in a biophoton. Without being bound to any theories, a biophoton disclosed herein can penetrate the human body up to more than, less than, or equal to about: 0.5 inches, 1 inch, 2 inches, 3 inches, 4 inches, 5 inches, 6 inches, 7 inches, or 8 inches. In some cases, far infrared light can penetrate into the muscles, tissues, joints, and more. In some embodiments, biophotons can be produced by a medical device. In some cases, a biophoton can be produced at least in part by non-living material, such as inorganic material. In some cases, a biophoton can be produced at least in part by an organic material.

As used herein, a "dose" can refer to a measured quantity of a therapeutic agent to be taken or administered at one time.

As used herein, the term "unit dose" or "dosage form" may be used interchangeably and may be meant to refer to pharmaceutical drug products or other therapies in the form in which they are marketed for use, with a specific mixture of active ingredients and inactive components, in a particular configuration, and apportioned into a particular dose to be delivered. The term "unit dose" may also sometimes encompass non-reusable packaging. More than one unit dose may refer to distinct pharmaceutical drug products packaged together, or to a single pharmaceutical drug product containing multiple drugs and/or doses. Types of unit doses may vary with the route of administration for drug delivery, and the substance(s) being delivered.

As used herein, the terms "effective amount" or "therapeutically effective amount" of a therapy used to treat a disease may be an amount and/or duration of a therapy that may reduce the severity of a disease, reduce the severity of one or more symptoms associated with the disease or its treatment, or delay the onset of more serious symptoms of a disease. An "effective amount" may be determined empirically and in a routine manner, in relation to the stated purpose The term "substantially" or "essentially" can refer to a qualitative condition that exhibits an entire or nearly total range or degree of a feature or characteristic of interest. In some cases, substantially can refer to a total range or degree of a feature or characteristic of interest by about plus or minus 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some cases, substantially can refer to at least about: 70%, 75%, 80%, 85%, 90%, 95%, 99%, or 100% of the total range or degree of a feature or characteristic of interest.

The section headings used herein are for organizational purposes only and are not to be construed as limiting the subject matter described.

Medical Device

In some embodiments, a medical device can be referred to as a biophoton generator. In some embodiments, a medical device can be referred to as a bioenergy generator. In some embodiments, a biophoton generator can comprise a medical device. In some embodiments, a bioenergy generator can comprise a medical device. The medical device disclosed herein can include a stone, such as a diamond, an amethyst, a tourmaline, a jade, an obsidian, or any combination thereof. In some embodiments, a medical device herein can comprise a polymer such as a rubber. In some embodiments, a medical device herein can comprise a sand. In some embodiments, a medical device herein can comprise a metal and/or an alloy. In some instances, a medical device herein can comprise a stone, a sand, a polymer, a metal (or alloy), a water, or any combination thereof. In some cases, a medical device herein can comprise a supporting material to support a mixture of components. In some cases, an ingredient herein in a medical device can be further activated by using a larger medical device on an ingredient. In some embodiments, a medical device can substantially constantly generate and release biophotons in a 3 dimensional field.

In some embodiments, a medical device herein can comprise a stone. In some cases, a medical device herein can comprise a mix of stones, for example 1, 2, 3, 4, 5 or more types of stones. In some cases, a particle size of a stone in a medical device can have a diameter of about 0.01 mm to about 5 mm. In some cases, a particle size of a stone in a medical device can have a diameter of about 0.1 mm to about 5 mm. In some cases, a particle size of a stone in a medical device can have a diameter of more than, less than or equal to about: 0.1 mm, 0.5 mm, 1 mm, 2 mm, 3 mm, 4 mm or 5 mm. In some cases, a stone can comprise an amethyst, a tourmaline, a jade, an obsidian, or any combination thereof. In some cases, amethyst can have a trigonal crystal system and/or a Mohs Hardness value of about 7. In some cases, tourmaline can have a trigonal crystal system and/or a Mohs Hardness value of about 7-7.5. In some cases, jade can have a monoclinic crystal system and/or a Mohs Hardness value of about 6-7. In some cases, obsidian can have a spherulites and/or a Mohs Hardness value of about 5-6. In some cases, tourmaline and jade can produce negative ions when it is heated up or at room temperature. For example, tourmaline can produce more than about 1500 negative ions per cubic centimeter when heated. In another example, when heated jade can produce around 700 negative ions per cubic centimeter. Tourmaline can be superconductive and can generate a natural infrared wave. In some cases, a jade can be a black jade, a blue jade, a green jade, a nephrite jade, a jadeite jade, an orange jade, a purple jade, a red jade, or any combination thereof.

In some embodiments, a medical device herein can comprise a polymer. In some cases, a medical device herein can comprise a mix of polymers, for example 1, 2, 3, 4, 5 or more types of polymers. In some cases, a polymer herein is a rubber. In some cases, a polymer herein can comprise a cellulose. In some cases, a polymer herein can comprise a polysaccharide. In some cases, a cellulose can comprise a cellulose I, a cellulose II, a cellulose III, a cellulose IV, a salt of any of these, or any combination thereof. In some cases, a cellulose can comprise an alpha cellulose or a salt thereof. In some cases, a cellulose can comprise a beta cellulose, a gamma cellulose, or both. In some cases, a cellulose can comprise a hemicellulose, a cellulose ester, a cellulose ether, a salt of any of these, or any combination thereof. In some cases, a polysaccharide can comprise a hyaluronic acid, or a salt thereof. In some cases, a polysaccharide can comprise a starch, a glycogen, a galactogen, an inulin, an arabinoxylan, a chitin, a pectin, a heparin, a peptidoglycan, a salt of any of these, or any combination thereof. In some cases, the rubber can comprise an isoprene. In some cases, a rubber herein can be polymer of isoprene. In some cases, a rubber herein can be polymer of butyl. In some cases, a rubber herein can comprise a styrene-butadiene, a butyl, a nitrile, an ethylene propylene diene monomer, a silicone, a polyurethane, a hydrogenated nitrile, or any combination thereof. In some cases, the rubber can be a natural rubber. In some cases, a particle size of a polymer in a medical device can have a diameter of about 0.01 mm to about 5 mm or about 1 mm to about 2 mm. In some cases, a particle size of a polymer in a medical device can have a diameter of about 0.1 mm to about 5 mm. In some cases, a particle size of a polymer in a medical device can have a diameter of more than, less than or equal to about: 0.1 mm, 0.5 mm, 1 mm, 2 mm, 3 mm, 4 mm or 5 mm.

In some embodiments, a medical device herein can comprise a metal or an alloy. In some cases, a medical device herein can comprise a mix of metals or alloys, for example 1, 2, 3, 4, 5 or more types of metals or alloys. In some cases, a metal can be in the form of a powder. In some cases, a particle size of a metal or alloy in a medical device can have a diameter of about 0.01 mm to about 5 mm. In some cases, a metal can be in the form of a powder. In some cases, a particle size of a metal or alloy in a medical device can have a diameter of about 0.1 mm to about 5 mm. In some cases, a particle size of a metal or alloy in a medical device can have a diameter of more than, less than or equal to about: 0.1 mm, 0.5 mm, 1 mm, 2 mm, 3 mm, 4 mm or 5 mm. In some cases, a metal can comprise a copper, an iron, or both. In some cases, a metal or alloy can comprise an iron, a copper, a zinc, an aluminum, a calcium, a magnesium, a silver, a gold, a steel, or any combination thereof.

In some embodiments, a medical device herein can comprise a sand. In some cases, a medical device herein can comprise a mix of sands, for example 1, 2, 3, 4, 5 or more types of sands. In some cases, the sand can comprise silicon dioxide. In some cases, the sand is substantially comprised of silicon dioxide by weight. In some cases, a sand can comprise at least about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% silicon dioxide by weight. In some cases, a sand can comprise at least about 95% silicon dioxide by weight. In some cases, the sand comprises 100% silicon dioxide by weight. In some cases, a sand can comprise about: 1% to about 100%, 50% to about 100%, 75% to about 100%, 80% to about 100%, or 90% to about 100% of silicon dioxide by weight. In some cases, a particle size of a sand in a medical device can have a diameter of about 0.01 mm to about 5 mm. In some cases, a particle size of a sand in a medical device can have a diameter of about 0.1 mm to about 5 mm. In some cases, a particle size of a sand in a medical device can have a diameter of more than, less than, or equal to about: 0.1 mm, 0.5 mm, 1 mm, 2 mm, 3 mm, 4 mm or 5 mm.

In some embodiments, a medical device herein can comprise a water. In some cases, a water can be collected from a natural source. In some cases, a water herein can comprise a mix of natural water, for example 1, 2, 3, 4, 5 or more types of natural water can be mixed. In some cases, a water can be a distilled water.

In some embodiments, a medical device can comprise supporting material. In some cases, a supporting material can comprise a grout. In some cases, a supporting material can comprise a concrete. In some cases, a supporting material can comprise an agar. In some cases, an agar can comprise an agar from a seaweed. In some cases, an agar is a food grade agar. In some cases, a supporting material can comprise a sulfur cement such as a modified sulfur cement. In some cases, a supporting material can comprise a cement and/or a polymer. In some cases, a supporting material can comprise adhesive composition. In some cases, a supporting material does not contribute to the production of biophotons in a medical device. In some cases, a supporting material can contribute to the production of biophotons in a medical device.

In some embodiments, a medical device disclosed herein can continually generate biophotons for at least: 6 months, 1 year, 2 years, 3 years, 4 years, 5 years, 6 years, 7 years, 8 years, 9 years, or 10 years without adding any extra energy source. In some embodiments, the biophotons produced can penetrate the wall of the container, such as a metal container or a plastic container. In some cases, a biophoton can be detected outside of a container. In some cases, the medical device is active at room temperature and at temperatures less than room temperature or greater than room temperature. In some cases, the medical device is active at a temperature of more than, less than, or equal to about: 0° C., 1° C., 2° C., 3° ° C., 4° ° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° ° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° ° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° ° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° ° C., 90° ° C., 91° C., 92° ° C., 93° C., 94° C., 95° C., 96° C., 97° C., 98° C., 99° C., or 100° C.

In some embodiments, a medical device can be produced by methods disclosed herein. In some instances, materials for a biophoton can be selected, which can comprise: 1) a stone or a mix of stones; 2) a polymer such as a rubber; 3) a sand; 4) a metal; 5) a water; 6) a supporting material such as a grout; 7) or any combination thereof.

Each different material in the medical device can be of the same size or be different sizes. Each individual material in the medical device can be of the same size or be different sizes. In some case, the ingredient can be in the form of small pieces of a material. For example, the material can be in the form of a granule, a particle, a grain, or a fragment. In some cases, raw material can be processed to be similar in size. For example, a material can be manufactured to have a particle diameter of about 0.01 mm to about 5 mm or about 0.1 mm to about 5 mm. In some cases, the material can be in the shape of a sphere, an oval, an amorphous shape, a cube, a crystalline structure, or any combination thereof. In some cases, the diameter or the radius of a material can comprise from about: 0.001 mm to about 1000 mm, 0.001 mm to about 0.01 mm, 0.01 mm to about 1 mm, 0.01 mm to about 5 mm, 0.1 mm to about 5 mm, 0.1 mm to 50 mm, 0.1 mm to about 100 mm, 1 mm to about 100 mm, 0.5 mm to about 50 mm, 1 mm to about 25 mm, or about 0.1 mm to about 10 mm. In some cases, the diameter or the radius of a material can comprise more than about, less than about, or equal to about: 0.01 mm, 0.02 mm, 0.03 mm, 0.04 mm, 0.05 mm. 0.06 mm, 0.07 mm, 0.08 mm, 0.09 mm, 0.1 mm, 0.2 mm, 0.3 mm, 0.4 mm. 0.5 mm. 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, 110 mm, 00 mm, 120 mm, 140 mm, 160 mm, 180 mm, 200 mm, 220 mm, 240 mm, 260 mm, 280 mm, 300 mm, 320 mm, 340 mm, 360 mm, 380 mm, 400 mm, 420 mm, 440 mm, 460 mm, 480 mm, or 500 mm. In some cases, the length, width, or height of a material can comprise from about: 0.001 mm to about 1000 mm, 0.001 mm to about 0.01 mm, 0.01 mm to about 1 mm, 0.01 mm to about 5 mm, 0.1 mm to 50 mm, 0.1 mm to about 100 mm, 1 mm to about 100 mm, 0.5 mm to about 50 mm, 1 mm to about 25 mm, or about 0.1 mm to about 10 mm. In some cases, the length, width, or height of a material can comprise more than about, less than about, or equal to about: 0.01 mm, 0.02 mm, 0.03 mm, 0.04 mm, 0.05 mm. 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, 110 mm, 00 mm, 120 mm, 140 mm, 160 mm, 180 mm, 200 mm, 220 mm, 240 mm, 260 mm, 280 mm, 300 mm, 320 mm, 340 mm, 360 mm, 380 mm, 400 mm, 420 mm, 440 mm, 460 mm, 480 mm, or 500 mm. In some embodiments, small particles can be preferred over large particles. In some instances, the use of large particles can reduce the amount of biophotons produced by a medical device as compared to the use of small particles in a medical device.

In some cases, the materials in a medical device can be activated. In some cases, the materials in a medical device can be unactivated. In some embodiments, the materials of a medical device can be activated to produce additional biophotons as compared to unactivated materials. In some instances, the materials (e.g., the stones, sands, metal, polymer and/or water) can be activated by placing next to a strong field formed by using one or more medical devices. In some cases, the unactivated materials can be placed near the medical device for at least about: 2 hours, 4 hours, 6 hours, 8 hours, 10 hours, 12 hours, 16 hours, 24 hours, 48 hours, 72 hours, 4 days, 5 days, 6 days, 7 days, 8 days, 9 days, 10 days, 11 days, 12 days, 13 days, or 14 days to become activated.

In some embodiments, the materials can be weighed to achieve an exemplary ratio of activated materials. In some cases, a stone, a sand, a metal, and a water can be in a weight to weight ratio of about: 10%: 10%:10%:10%, and unactivated material at about 60%. For example, if the net weight of the content of the medical device is 1000 g (1 kg), then said ingredients of a stone, a sand, a metal, and a water can be 100 g, 100 g, 100 g, 100 g and unactivated material is 600 g. In some cases, a stone, a sand, a metal, a polymer, and a water can be in a weight to weight ratio of about: 10%:10%: 10%:10%:10% and unactivated material at about 50%. The ratio can be varied in a range. In some cases, a stone, a sand, a metal, and a water can be in a weight to weight ratio of about: 1%: 1%:1%:1% and unactivated material at about 96%. In some cases, a stone, a sand, a metal, a polymer, and a water can be in a weight to weight ratio of about: 1%: 1%:1%:1%:1% and unactivated material at about 95%. In some cases, a stone, a sand, a metal, and a water can be in a weight to weight ratio of about: 5%:5%:5%:5% and unactivated material at about 80%. In some cases, a stone, a sand, a metal, a polymer, and a water can be in a weight to weight ratio of about:

5%:5%:5%:5%:5% and unactivated material at about 75%. In some cases, a stone, a sand, a metal, and a water can be in a weight to weight ratio of about: 15%: 15%:15%:15% and unactivated material at about 40%. In some cases, a stone, a sand, a metal, a polymer, and a water can be in a weight to weight ratio of about: 15%: 15%: 15%: 15%:15% and unactivated material at about 25%. In some cases, a polymer, a stone, a sand, a metal, and a water can be in a weight to weight ratio of about: 50% (polymer): 10% (stone): 10% (sand):10% (metal): 10% (water) and unactivated material at about 10%. In some cases, a stone, a sand, a metal, a polymer, and/or a water can be in an equal weight to weight ratio. In some cases, a stone, a sand, a metal, a polymer, a water, and/or a supporting material can be in an equal weight to weight ratio. In some cases, the ratio can be varied in a range that those said ingredients of a stone, a sand, a metal, a polymer, and a water can be in a weight to weight ratio of 1% for one material and 1-99% for the other materials and 1-99% for the unactuated materials for a weight to weight ratio total of 100%. In some cases, a stone, a sand, a metal, a polymer, and/or a water can be in a weight to weight ratio with the other ingredients (e.g., a stone, a sand, a metal, a polymer, and/or a water and unactive materials) and be in an amount of about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, or 97% for a weight to weight ratio total of 100%. In some cases, a stone, a sand, a polymer, a metal, and/or a water can be added to a mixture in a specific amount. For example, a stone, a sand, a polymer, a metal, and/or a water can be added in an amount that ranges from about: 1 mg to about 10 grams, 1 gram to about 10,000 grams, 1 gram to about 1,000 grams, 10 gram to about 100 grams, 50 grams to about 250 grams, 100 grams to about 1,000 grams, or about 1,000 grams to about 10,000 grams. In some cases, a stone, a sand, a polymer, a metal, and/or a water can be added in an amount of more than, less than, or equal to about: 1 mg, 10 mg, 100 mg, 1 gram (g), 5 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, 150 g, 200 g, 250 g, 300 g, 350 g, 400 g, 450 g, 500 g, 550 g, 600 g, 650 g, 700 g, 750 g, 800 g, 850 g, 900 g, 950 g, 1000 g, 1100 g, 1200 g, 1300 g, 1400 g, 1500 g, 1600 g, 1700 g, 1800 g, 1900 g, 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g, 3600 g, 3700 g, 3800 g, 3900 g, 4000 g, 4100 g, 4200 g, 4300 g, 4400 g, 4500 g, 4600 g, 4700 g, 4800 g, 4900 g, 5000 g, 5100 g, 5200 g, 5300 g, 5400 g, 5500 g, 5600 g, 5700 g, 5800 g, 5900 g, 6000 g, 6100 g, 6200 g, 6300 g, 6400 g, 6500 g, 6600 g, 6700 g, 6800 g, 6900 g, 7000 g, 7100 g, 7200 g, 7300 g, 7400 g, 7500 g, 7600 g, 7700 g, 7800 g, 7900 g, 8000 g, 8100 g, 8200 g, 8300 g, 8400 g, 8500 g, 8600 g, 8700 g, 8800 g, 8900 g, 9000 g, 9100 g, 9200 g, 9300 g, 9400 g, 9500 g, 9600 g, 9700 g, 9800 g, 9900 g, or 10000 g.

In some embodiments, the materials for a medical device can be contacted and/or mixed together. In some cases, the materials are mixed in a substantially heterogeneous or substantially homogeneous mixture. In some cases, one or more of a stone, a sand, a metal, a polymer, a water, and an unactivated material are mixed. In some cases, the material are mixed by a mixer. In some cases, an unactivated ingredient is first added to the mixer then the activated materials are added to the mixer to create a mixed composition. In some cases, an activated material is first added to the mixer then the unactivated material is added to the mixer to create a mixed composition. In some cases, activated materials and unactivated materials are added to the mixer at the same time to create a mixed composition. In some cases, the substantially solid structure can be solidified after the materials are mixed together by different inactive materials such as grouts. In some cases, the medical device can produce biophotons day and night automatically and consistently without the use of other energy resources, such as electricity, light, or heat.

In some embodiments, the materials for a medical device can be added into or to a container. In some cases, the materials are substantially mixed prior to adding the materials to a container. In some cases, a container can be a stainless steel container or a plastic container. In some cases, a container can be a glass container or an organic container such as a wood container. In some cases, the container comprises a stainless steel container, an aluminum container, or a mixture of both. In some cases, a container can be a mix of materials. In some cases, a container is a closed container. In some cases, a container is a sealed container. In some cases, the container may not substantially contribute to the production of biophotons. In some cases, the container may contribute to the production of biophotons. Any shape of container can be used. In some cases, the net weight of the mix of materials can range from about: 1 gram to about 100 kg, 10 grams to about 100 kg, 1 gram to about 10 grams, 10 grams to about 100 grams, 50 grams to about 500 grams, 100 grams to about 1 kg, 500 grams to about 5 kg, 1 kg to about 20 kg, 1 kg to about 10 kg, 5 kg to about 25 kg, 20 kg to about 50 kg, or 50 kg to about 100 kg. In some cases, the net weight of the mix of materials can be more than, less than, or equal to about: 1 gram, 5 grams, 10 grams, 20 grams, 30 grams, 40 grams, 50 grams, 60 grams, 70 grams, 80 grams, 90 grams, 100 grams, 200 grams, 300 grams, 400 grams, 500 grams, 600 grams, 700 grams, 800 grams, 900 grams, 1000 grams, 1 kg, 2 kg, 3 kg, 4 kg, 5 kg, 6 kg, 7 kg, 8 kg, 9 kg, 10 kg, 11 kg, 12 kg, 13 kg, 14 kg, 15 kg, 16 kg, 17 kg, 18 kg, 19 kg, 20 kg, 25 kg, 30 kg, 35 kg, 40 kg, 45 kg, 50 kg, 55 kg, 60 kg, 65 kg, 70 kg, 75 kg, 80 kg, 85 kg, 90 kg, 95 kg, or 100 kg.

In some cases, a medical device can have a total filled or unfiled volume of about: 100 ml to about 10,000 ml, 240 ml to about 5,760 ml, about 200 ml to about 8,000 ml, 100 ml to about 1000 ml, 500 ml to about 5,000 ml, 1,000 ml to about 8,000 ml, 2,000 ml to about 6,000 ml or 5,000 ml to about 10,000 ml. In some cases, a medical device can have a total filled or unfiled volume of more than, less than, or equal to about: 10 ml, 100 ml, 200 ml, 240 ml, 300 ml, 400 ml, 500 ml, 600 ml, 700 ml, 800 ml, 900 ml, 1000 ml, 1100 ml, 1200 ml, 1300 ml, 1400 ml, 1500 ml, 1600 ml, 1700 ml, 1800 ml, 1900 ml, 2000 ml, 2100 ml, 2200 ml, 2300 ml, 2400 ml, 2500 ml, 2600 ml, 2700 ml, 2800 ml, 2900 ml, 3000 ml, 3100 ml, 3200 ml, 3300 ml, 3400 ml, 3500 ml, 3600 ml, 3700 ml, 3800 ml, 3900 ml, 4000 ml, 4100 ml, 4200 ml, 4300 ml, 4400 ml, 4500 ml, 4600 ml, 4700 ml, 4800 ml, 4900 ml, 5000 ml, 5100 ml, 5200 ml, 5300 ml, 5400 ml, 5500 ml, 5600 ml, 5700 ml, 5,760 ml, 5800 ml, 5900 ml, or 6000 ml.

In some embodiments, the biophotons produced by a medical device are produced in a three-dimensional field and can penetrate body of a subject. In some cases, the biophotons produced by a medical device are effective and/or active on a subject at a distance in a range of about: 0.1 meter to about 20 meters, 0.1 meters to about 1 meter, 0.5 meter to about 3 meters, 1 meter to about 10 meters, 0.5 meter to 5 meters, 2 meters to 8 meters, 5 meters to about 15 meters or about 10 meters to about 20 meters. In some cases, the biophotons produced by a medical device are effective and/or active on a subject at a distance of more than, less than, or equal to about: 0.1 meters, 0.2 meters, 0.3 meters, 0.4 meters, 0.5 meters, 0.6 meters, 0.7 meters, 0.8 meters, 0.9 meters, 1 meters, 2 meters, 3 meters, 4 meters, 5 meters, 6 meters, 7 meters, 8 meters, 9 meters, 10 meters, 11 meters, 12 meters, 13 meters, 14 meters, 15 meters, 16 meters, 17 meters, 18 meters, 19 meters, or 20 meters. In some cases, the biophotons can be active on direct contact with a subject, for example if a subject is touching a medical device. In some instances, the strength of the photon field can correlate with the size of the device and the closeness from the user. For example, a medical device produces a larger biophoton dose when the subject is closer to the medical device.

In some embodiments, the biophotons produced by a medical device can be measured with a biophoton detector. In some cases, in order to measure the production of biophotons the device must produce at least about 500 or 1000 biophotons per second.

In some cases, biophotons can be measured at least in part by low-consumption high-sensitivity Complementary Metal Oxide Semiconductor (CMOS) sensors. In some cases, CMOS sensors can have resolution in the UV spectrum visual range and infrared range.

In some cases, a biophotons can be measured by a MIRA camera. In some cases, a biophoton can be detected and/or measured with a photomultiplier or by a CCD camera (e.g., an ultra-low noise CCD camera). In some cases, a biophoton can be measured with a single photon detector. In some cases, a MIRA camera can be a Model 800, MIRA digital multispectral video-camera manufactured by The Daniele Gullà Laboratory, Ecole Universitarie, Bologna, Italy. The MIRA camera, used herein to capture photon and biophoton emissions, is a digital multispectral video camera. In some cases, it can record, process, and save ultraviolet/visible/near infrared spectroscopy (UV-vis-NIR images) and communicate with remote devices. The video camera collects different frames and quickly compares the frames pixel by pixel. In case of minor variations, the system amplifies the weak signal with a series of mathematical elaborations, namely a fast Fourier transform (FFT) pyramidal algorithm that paints the monochromatic parts in black and white while following a fixed color code scale. As a result, the electromagnetic field variation and the photon flux increase exponentially. The unstable flux is produced by micro-variations and oscillations of the optical field (luminance and chrominance), which are likely to be of a quantum nature.

Treatment of Diseases and Conditions

Disclosed herein are diseases and conditions that can be treated with a biophoton therapy. In some cases, the biophoton therapy can be administered by a medical device. In some cases, a biophoton therapy can be used to supplement and/or improve the health of a subject. In some cases, a biophoton therapy herein can be used to treat a symptom of a disease or condition.

In some cases, a biophoton therapy disclosed herein can increase a blood circulation, remove a metabolic waste, treat a pain of a muscle, treat a joint pain, treat a muscle and/or joint stiffness, treat a joint pain associated with an arthritis, relieve a muscle spasm, treat a muscle strain, treat a muscular back pain, provide a muscle relaxation, or any combination thereof. In some cases, a biophoton therapy disclosed herein can be used to treat muscle pain, treat a pain, treat a head ache, treat a muscle tension, treat a chronic pain, or any combination thereof. In some cases, a pain can be a back pain. In some cases, a pain can comprise an acute pain, a chronic pain or both. In some cases, a pain can comprise a neuropathic pain, a nociceptive pain, a radicular pain, or any combination thereof.

In some cases, a biophoton therapy disclosed herein can be used to treat a migraine. In some cases, a migraine can comprise a hemiplegic migraine, an abdominal migraine, a vestibular migraine, a menstrual migraine, a migraine with brainstem aura, a medication overuse headache, a status migrainosus, a cluster headache, a sinus headache, a caffeine headache, or any combination thereof.

In some cases, a biophoton therapy disclosed herein can be used to treat an arthritis. In some cases, an arthritis can comprise a rheumatoid arthritis. In some cases, an arthritis can comprise an osteoarthritis, a gout, a fibromyalgia, a childhood arthritis, an infectious arthritis, a psoriatic arthritis, an ankylosing spondylitis, or any combination thereof.

In some cases, a composition herein can be administered to improve focus, improve a mood, promote brain health, and/or provide energy. In some cases, a biophoton therapy disclosed herein can be used to improve circulation, improve breathing, reduce inflammation, accelerate wound healing, normalize frequency of urination, or any combination thereof. In some cases, a biophoton therapy can be used to increase the intelligence level of a subject. In some cases, a biophoton therapy can be used to improve a strength, a mental exhaustion, a physical exhaustion, a libido, or any combination thereof of a subject. In some cases, a medical device can be used to enhance an athletic ability. In some cases, the subject can have a low IQ level. In some cases, a medical device can be used to improve the ability to focus.

In some cases, a medical device herein can be used to treat a subject with a chronic fatigue, an insomnia, a mental condition, or any combination thereof. In some cases, a medical device herein can be used to treat a stress, treat a fatigue, or both. In some cases, a stress can be an acute stress, a chronic stress, a physical stress, a phycological stress, or any combination thereof. In some cases, a chronic fatigue system can comprise a physical exhaustion, a mental exhaustion, a difficulty walking or any combination thereof.

In some cases, a biophoton therapy herein can be used to treat a symptom of a disease or condition. In some cases, a symptom of a disease or condition can comprise a fatigue, feeling tired weakness, brain fog (problems concentrating or thinking), a headache, a tremor, a rapid or pounding heartbeat, a feeling of skipped heartbeats (e.g., palpitations), a dizziness upon standing, a symptoms that worsen after physical or mental activity (e.g., as post-exertional malaise).

In some cases, biophoton therapy disclosed herein can be used to treat a sleep disorder. In some cases, a biophoton therapy disclosed herein can increase sleep duration of a subject. In some cases, a sleep disorder can comprise restless legs syndrome, narcolepsy, a sleep apnea, a parasomnia, a sleep paralysis, a hypersomnia, a sleep walking disorder, a nightmare disorder, a bruxism or any combination thereof. In some cases, biophoton therapy disclosed herein can be used to treat an insomnia. In some cases, biophoton therapy disclosed herein can be used to treat a chronic fatigue syndrome. In some cases, biophoton therapy disclosed herein can be used to treat a chronic pain, an acute pain, a mild pain, a moderate pain, a severe pain, a very severe pain, and/or a worst possible pain.

In some cases, biophoton therapy disclosed herein can be used to treat a mental disorder. In some cases, a mental disorder can comprise an anxiety disorders, a behavioral disorder, an emotional disorder, a bipolar disorder, a depression, a dissociation disorder, a dissociative disorder, an eating disorder, an obsessive compulsive disorder, a paranoia disorder, a post-traumatic stress disorder (PTSD), a psychosis, a schizophrenia, or any combination thereof. In some cases, biophoton therapy disclosed herein can be used to treat an attention-deficit-hyperactivity disorder (ADHD). In some cases, a mental health disorder can comprise a generalized anxiety disorder, a social phobia, an agoraphobia, a claustrophobia, a panic disorder, an obsessive compulsive disorder (OCD), an autism, an oppositional defiant disorder, a conduct disorder, an anorexia, a major depression, a persistent depressive disorder, a bipolar disorder, a seasonal affective disorder, a postpartum depression, a premenstrual dysphoric disorder, an atypical depression, a treatment resistant depression, a bulimia nervosa, or any combination thereof. In some cases, biophoton therapy disclosed herein can be used to treat an autism.

In some cases, a medical device herein can be used to treat a wound and/or accelerate wound healing. In some cases, a wound can be a surgical wound. In some cases, a wound can be a wound from a battlefield or from an accident such as a car accident. In some cases, a medical device can be used to increase wound healing speed, for example for those who have surgery as compared to a wound not exposed to a medical device.

In some cases, a biophoton therapy can be used to treat a stroke. In some cases, a stroke is a chronic stroke. In some cases, a stroke is an acute stroke. In some cases, a stroke can comprise a ischemic stroke, a hemorrhagic stroke, a transient ischemic attack (e.g., a mini stroke), a brain stem stroke, a cryptogenic stroke, or any combination thereof. In some cases, biophoton therapy disclosed herein can be used to treat a paralysis (e.g., paralysis after a stroke). In some cases, a biophoton therapy can be used to treat a stroke or a stroke-paralysis.

In some cases, biophoton therapy disclosed herein can be used to treat a dementia. In some cases, a dementia can comprise an Alzheimer's disease, a vascular dementia, a Lewy Body disease, a frontotemporal dementia, an alcohol related dementia, an HIV associated dementia, a chronic traumatic encephalopathy (CTE) dementia, a childhood dementia, a mixed dementia, or any combination thereof. In some cases, biophoton therapy disclosed herein can be used to treat an Alzheimer's disease, a dementia pugilistica, traumatic brain injury, a Parkinson's disease, or any combination thereof. In some cases, a biophoton therapy can be used to reverse the loss of a cognitive ability such as the loss of a cognitive ability due to a dementia. In some cases, a biophoton therapy can be used to substantially stop the loss of a cognitive ability such as the loss of a cognitive ability due to a dementia. In some cases, biophoton therapy disclosed herein can be used to treat a multiple sclerosis. In some cases, a biophoton therapy can be used to promote brain cell function.

In some cases, biophoton therapy disclosed herein can be used to treat a cardiac disorder. In some cases, a cardiac disorder can comprise a coronary heart disease, an angina, a unstable angina, a heart attack, a heart failure, an arrhythmia, a valve disease, a high blood pressure, a congenital heart condition, an inherited heart condition, or any combination thereof. In some cases, biophoton therapy disclosed herein can be used to treat a hypertension. In some cases, biophoton therapy disclosed herein can be used to treat a heart disease and/or a heart failure.

In some cases, biophoton therapy disclosed herein can be used to treat a liver disease. In some cases, biophoton therapy disclosed herein can be used to treat a cirrhosis and/or a hepatitis. In some cases, biophoton therapy disclosed herein can be used to treat a kidney deficiency. In some cases, biophoton therapy disclosed herein can be used to treat a kidney disease. In some cases, a kidney disease can comprise a glomerulonephritis, a kidney stone, a kidney failure, a urinary tract infection, a lupus, a polycystic kidney disease, an Alport syndrome, an ectopic kidney, a Fabry disease, an analgesic nephropathy, a kidney cancer, a nephronophthisis, a vasculitis, an acute tubular necrosis, an APOL1-related nephropathy, a hemolytic uremic syndrome, an inherited FSGS syndromes, an interstitial nephritis, a kidney cyst, or any combination thereof. In some cases, biophoton therapy disclosed herein can be used to treat a diabetes. In some cases, a diabetes can be a type 1 diabetes or a type 2 diabetes.

In some cases, biophoton therapy disclosed herein can be used to treat diseases and conditions such a viral disease, a bacterial disease, a parasitic disease, or any combination thereof. In some cases, a viral disease is a SARS infection such as SARS-COV-2, an influenza infection, a rhinovirus infection, or any combination thereof. In some cases, a medical device can be used to increase an immune response. In some cases, a biophoton therapy can be used to treat a long coronavirus disease 2019 (COVID-19), a COVID-19 disease, a Coronavirus disease, or any combination thereof. In some cases, a biophoton therapy herein can be used to treat an autoimmune disorder. In some cases, a biophoton therapy can be used to treat a Lyme disease.

In some cases, biophoton therapy disclosed herein can be used to treat an anemia. In some cases, an anemia can be due to chemotherapy and/or radiotherapy. In some cases, a biophoton therapy herein can alter a skin temperature, a blood oxygen level, or both. For example, a biophoton therapy herein can increase a skin temperature of a subject, increase a blood oxygen level of a subject (as measured by a pulse-oximeter), or both.

In some cases, biophoton therapy disclosed herein can be used to treat a gynecological dysmenorrhea, a premenstrual syndrome (PMS), an infertility, or any combination thereof. In some cases, a biophoton therapy disclosed herein can be used to treat a male disease, such as a prostate enlargement, an erectile dysfunction, or any combination thereof.

In some cases, biophoton therapy disclosed herein can be used to treat a seizure disorder. In some cases, a seizure disorder can comprise an epilepsy, a tonic seizure, an atonic seizure, a myoclonic seizure, a clonic seizure, a generalized seizure, a focal seizure, a temporal lobe epilepsy, a Dravet syndrome, or any combination thereof.

In some cases, biophoton therapy disclosed herein can be used to improve bone health, for example in a subject who has an osteoporosis. In some cases, a biophoton therapy can be used to treat an osteoporosis. In some cases, a biophoton therapy can be used to treat a hip dysplasia.

In some cases, a biophoton therapy can be used to improve cellular activities of cerebral arteries, improve cellular activities of a neck vein, improve cellular activities of a retina, improve cellular activities of a major organ, improve cellular activities of a pancreas, improve cellular activities of a spleen, improve cellular activities of a kidney, improve cellular activities of an intestine, or any combination thereof. In some cases, the improvement can be compared against cellular activities of a cell, organ, or biological tissue that was not exposed to a biophoton therapy.

In some cases, a biophoton therapy can be used to reduce ageing in a subject, reduce the occurrence or wrinkles, blemishes or both. In some cases, a biophoton therapy can be used to treat an acne, a folliculitis, an acne scars, an aging skin, a blemish, a broken blood vessel, a brown spots, a discolored skin, a crease, a deflated or sinking (e.g., around cheeks, temples, lips and eyes), a dull skin, a discolored skin, a fatigued appearance, a tired appearance, a fine line, a fine crease, a flaking skin, a cracking skin, a flushed appearance, a freckle, a furrow, a or a crinkle, a skin rash, a hirsutism, a hypertrichosis, a hyperpigmentation, a rosacea, a sagging or loss of volume, a scarring of a skin, a spider vein, a skin textural change, a wrinkle, or any combination thereof. In some cases, a biophoton therapy can be used to induce stem cell proliferation to replace those aged, injured, or diseases cells.

In some cases, a biophoton therapy can be used to treat an eye disorder. In some cases, the eye disorder can be glaucoma. In some cases, a glaucoma can comprise a tension glaucoma, a congenital glaucoma, a pigmentary glaucoma, a primary glaucoma, an open-angle glaucoma, a normal-tension glaucoma, an angle-closure glaucoma, a neovascular glaucoma, an exfoliation glaucoma, a uveitic glaucoma, or any combination thereof. In some cases, a biophoton therapy can improve a retina. In some cases, the improved retina can increase visual function, and blood circulation in an eye.

In some cases, a biophoton therapy can be used to treat a mitochondrial deficiency. In some cases, a biophoton therapy can be used to treat a mitochondrial disease. In some cases, a mitochondrial disease can comprise a mitochondrial encephalopathy, a lactic acidosis and stroke-like episodes (MELAS) syndrome, a Leber hereditary optic neuropathy, a Leigh syndrome, a Kearns-Sayre syndrome, a Myoclonic epilepsy and ragged-red fiber disease, an Alpers syndrome, a Pearson syndrome, a mitochondrial cardiomyopathy, a Barth syndrome, a lactic acidosis, or any combination thereof.

In some cases, a biophoton therapy can be used to treat an asthma, a Chronic Obstructive Pulmonary Disease (COPD), a respiratory disease, or any combination thereof. In some cases, a treatment of a respiratory disease can comprise an increase in breathing capacity after treatment as compared to the breathing capacity before a treatment. In some cases, a biophoton therapy can be used to treat a tinnitus. In some cases, a biophoton therapy can be used to treat a genetic disease. In some cases, a biophoton therapy can be used to treat a neuromuscular disease.

In some cases, a biophoton therapy can be used to treat a gastrointestinal disorder. In some cases a gastrointestinal disorder can comprise an irritable bowel syndrome, an ulcerative colitis, a Celiac disease, a constipation, an ulcer, a hemorrhoids, a diarrhea, a diverticulitis, a dyspepsia, an anal fissures, a bowel obstruction, a colon cancer, a gallstone, a gastroenteritis, a nausea, a pancreatitis, a bowel incontinence, a colorectal polyp, a gastric neoplasm, a gastritis, a short bowel syndrome, or any combination thereof. In some cases, a biophoton therapy can be used to treat a taste or smell disorder, a cough, a chest pain, a hearing problem (e.g., hearing loss or ringing in the ears), a shortness of breath, a hair loss, a sleep disorder, a bladder disorder, including difficulty urinating or incontinence, a vision problem (such as blurry vision, sensitivity to light, floaters, flashing lights, or difficulty reading or focusing eyes) a swelling of the legs, a problem with teeth, a foot pain, a change in menstrual cycle, or any combination thereof. In some cases, a bladder disorder can comprise a bedwetting, a cystitis, a bladder stone, an overactive bladder, a paruresis, an urinary incontinence, a cystocele, a bladder polyp, a bladder cancer, or any combination thereof.

In some cases, a biophoton therapy can be used to treat a thyroid disorder. In some cases, a thyroid disorder can comprise hyperthyroidism, hypothyroidism, or any combination thereof. In some cases, a medical device can be used to balance a hormone level, for example in a subject who has a hyperthyroid or hypothyroid function. In some cases, a biophoton therapy can be used to treat a Cushing's disease. In some cases, a biophoton therapy can be used to treat an endocrine disorder.

In some cases, a biophoton therapy can be used to treat delayed growth of a subject (e.g., a short stature), a delayed puberty, or both. In some cases, a biophoton therapy can be used to induce body growth (e.g., for a child who has a delayed growth). In some cases, a medical device can be used to increase a metabolism of a human.

In some cases, a medical device can be used to treat a cancer. In some cases, a cancer can be a terminal cancer. In some cases, a cancer can comprise a stage 1 cancer, a stage 2 cancer, a stage 3 cancer, or a stage 4 cancer. In some cases, a cancer can comprise a lung cancer, a colon cancer, a leukemia, a prostate cancer, a bone cancer, a breast cancer, a brain tumor, a pancreatic cancer, a stomach cancer, an ovary cancer, a uterus cancer, or any combination thereof. In some cases, treatment of a cancer can comprise reducing the size of a tumor, stopping the growth of a tumor, stopping the spread of a tumor, reduce side effects or toxicity of a chemotherapy or radiotherapy of a cancer, or any combination thereof. In some cases, a biophoton therapy can be used to treat a lymphedema. In some cases, a cancer can comprise an acute lymphoblastic leukemia (ALL), an acute myeloid leukemia (AML), an adolescent cancer, an adrenocortical carcinoma, an AIDS-related cancers, an AIDS-related lymphoma (e.g., a lymphoma), a primary CNS lymphoma (e.g., a lymphoma), an anal cancer, an appendix cancer, an astrocytoma (e.g., a brain cancer), an atypical teratoid, a rhabdoid tumor, a central nervous system cancer (e.g. brain cancer), a basal cell carcinoma of the skin, a bile duct cancer, a bladder cancer, a bone cancer (including an Ewing sarcoma and an osteosarcoma and an malignant fibrous histiocytoma), a sarcoma, a bronchial tumor (e.g., lung cancer), a Burkitt lymphoma, a carcinoma, an atypical teratoid, a rhabdoid tumor (e.g., brain cancer), an medulloblastoma and other CNS embryonal tumors, a germ cell tumor, a primary CNS lymphoma, a cervical cancer, a childhood cancer, a cancer of childhood (e.g., rare), a cholangiocarcinoma, Chordoma (e.g., bone cancer, a chronic lymphocytic leukemia (CLL), a chronic myelogenous leukemia (CML), a chronic myeloproliferative neoplasms, a colorectal cancer, a craniopharyngioma (e.g., brain cancer), a cutaneous T-cell lymphoma, a ductal carcinoma In Situ (DCIS), an embryonal tumor, a medulloblastoma, an endometrial cancer (e.g., uterine cancer), an ependymoma, an esophageal cancer, an esthesioneuroblastoma (e.g. head and neck cancer), an Ewing sarcoma (e.g., bone cancer), an extracranial germ cell tumor, an extragonadal germ cell tumor, an eye cancer, an intraocular melanoma, a retinoblastoma, a fallopian tube cancer, a gallbladder cancer, a gastric (stomach) cancer, gastrointestinal neuroendocrine tumors, gastrointestinal stromal tumors (GIST) (e.g., soft tissue sarcoma), a germ cell tumor, a childhood central nervous system germ cell tumors, an extracranial germ cell tumors, an extragonadal germ cell tumor, an ovarian germ cell tumor, a testicular cancer, a gestational trophoblastic disease, an hairy cell leukemia, a head and neck cancer, heart tumors, a hepatocellular (liver) cancer, an histiocytosis (e.g., langerhans cell), a Hodgkin lymphoma, a hypopharyngeal cancer (e.g., head and neck cancer), an intraocular melanoma, an islet cell tumor, a pancreatic neuroendocrine tumor, a soft tissue sarcoma, a kidney (renal cell) cancer, a Langerhans cell histiocytosis, a laryngeal cancer, an eye cancer, a leukemia, a lip and oral cavity cancer (e.g., head and neck cancer), a liver cancer, a lung cancer (e.g., non-small cell, small cell, pleuropulmonary blastoma, pulmonary inflammatory myofibroblastic tumor, and tracheobronchial tumor), a lymphoma, a male breast cancer, a melanoma, a melanoma (e.g., intraocular (Eye)), a Merkel cell carcinoma (e.g., skin cancer), a mesothelioma, a metastatic cancer, a metastatic squamous neck cancer with occult primary, a midline tract carcinoma with NUT gene changes, a mouth cancer (e.g., head and neck cancer), a multiple endocrine neoplasia syndrome, s multiple myeloma/plasma cell neoplasm, mycosis fungoides (e.g., lymphoma), myelodysplastic syndromes, myelodysplastic/myeloproliferative neoplasms, a myelogenous leukemia (CML) (e.g., chronic), a myeloid leukemia (AML) (e.g., acute), myeloproliferative neoplasms (e.g., chronic), a nasal cavity and paranasal sinus cancer, a nasopharyngeal cancer, a neuroblastoma, neuroendocrine tumors, a non-Hodgkin lymphoma, a non-small cell lung cancer, an oral cancer, a lip and oral cavity cancer and oropharyngeal cancer, a osteosarcoma and undifferentiated pleomorphic sarcoma of bone treatment, an ovarian cancer, a pancreatic cancer, pancreatic neuroendocrine tumors (e.g., an islet cell tumor), a papillomatosis (e.g., laryngeal), a paraganglioma, a paranasal sinus and nasal cavity cancer, a parathyroid cancer, a penile cancer, a pharyngeal cancer, a pheochromocytoma, a pituitary tumor, a plasma cell neoplasm/multiple myeloma, a pleuropulmonary blastoma, a pregnancy and breast cancer, a primary central nervous system (CNS) lymphoma, a primary peritoneal cancer, a prostate cancer, a pulmonary inflammatory myofibroblastic tumor, a rare cancer, a rectal cancer, a recurrent cancer, a renal cell cancer (e.g., kidney cancer), a retinoblastoma, a rhabdomyosarcoma (e.g., soft tissue sarcoma), a salivary gland cancer, a sarcoma, a childhood rhabdomyosarcoma, a childhood vascular tumor, a bone cancer, a Kaposi sarcoma, an osteosarcoma, a soft tissue sarcoma, a uterine sarcoma, a Sézary syndrome (e.g., lymphoma), a skin cancer, a small cell lung cancer, a small intestine cancer, a soft tissue sarcoma, a squamous cell carcinoma of the skin, a squamous neck cancer with occult primary, a stomach (gastric) cancer, a T-cell lymphoma (e.g., cutaneous), a testicular cancer, a throat cancer (e.g., head and neck cancer), a nasopharyngeal cancer, an oropharyngeal cancer, a hypopharyngeal cancer, a thymoma and thymic carcinoma, a thyroid cancer, tracheobronchial tumors (e.g., lung cancer), a transitional cell cancer of the renal pelvis and ureter (e.g., kidney cancer), an unknown primary, a ureter and renal pelvis (e.g., transitional cell cancer), a urethral cancer, a uterine cancer (e.g., endometrial), a uterine sarcoma, a vaginal cancer, a vascular tumor, a vulvar cancer, a Wilms tumor (e.g., kidney tumors), a cancer in young adults, or any combination thereof.

Additional Uses of Biophoton Therapy

In some embodiments, a biophoton therapy can be used to stimulate a biological process. For example, biophoton therapy can be used to simulate increased fermentation of a microbial system/culture, induce accelerated plant growth, increase cellular production of a biological material, promote growth of an animal, among other things.

In some embodiments, biophoton therapy can be used to increase the rate of fermentation, for example fermentation of an alcohol. In some cases, a fermentation can be in a fermentation tank. In some cases, the rate of fermentation by yeast (e.g., *Saccharomyces cerevisiae*) can be increased by biophoton therapy. In some cases, the rate of a fermentation after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a fermentation that is not administered a biophoton therapy. In some cases, the yield of a fermentation (e.g., yield of ethanol) can be increased by a biophoton therapy. In some cases, the yield of fermentation after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a fermentation that is not administered a biophoton therapy.

In some embodiments, administration of a biophoton therapy can be used to increase biological processes, for example administration of biophotons can increase the rate of protein production and/or molecule production from a cell. In some cases, the rate of a protein production from a cell after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a protein production from a cell that is not administered a biophoton therapy. In some cases, the rate of a compound produced from a cell after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a compound produced from a cell that is not administered a biophoton therapy. In some cases, administration of a biophoton therapy can increase the rate of therapeutic protein production by a cell. For example, the rate of antibody production by a cell can be increased by biophoton administration to the cell. In some cases, the yield of a protein and/or compound production by a cell can be increased by a biophoton therapy. In some cases, the yield of a protein and/or compound from a cell after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a yield of a protein and/or compound from a cell that is not administered a biophoton therapy.

In some cases, a medical device can be used to infuse a water, a beverage, a soda, and/or juices with biophotons. In some cases, a water or a beverage can be energized with biophotons produced by a medical device. In some cases, the biophotons can remain in the water and be administered by drinking a water or a beverage or by contacting a subject with the water. In some cases, a beverage can comprise an alcoholic beverage (e.g., a wine, a beer, or a liquor). In some cases, a beverage can comprise a juice, a soft drink, or any beverage. In some cases, a biophoton therapy can be used to increase the aging process/speed of a wine, liquor, or other beverage.

In some embodiments, a biophoton therapy can be used to promote the growth of an animal, such as a farm animal. In some cases, a farm animal can comprise chickens, ducks, pigs, sheep, cows, and/or horses. In some cases, biophoton therapy can be used to increase the weight of an animal. In some cases, the weight of an animal after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to the weight of an animal that is not administered a biophoton therapy. In some cases, a medical device can be used to enhance the growth of an animal, increase the production of a product (e.g., eggs) as compared to an animal not exposed to a medical device. In some cases, the egg production from an animal after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to the egg production from an animal that is not administered a biophoton therapy.

In some cases, a medical device can be used to increase the speed of growth, the yield, the shelf life, the nutritional value, or any combination thereof, of an agriculture product such as a fruit or a vegetable as compared to an agriculture product not exposed to a medical device. In some cases, the growth rate of a plant after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a growth grate of a plant that is not administered a biophoton therapy. In some cases, the yield of a crop of a plant (e.g., the total fruit/product produced) can be increased by a biophoton therapy. In some cases, the yield of a crop of a plant after or during biophoton therapy can be increased by at least about: 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% as compared to a yield of a crop of a plant that is not administered a biophoton therapy.

Administration

In some embodiments, a medical device as disclosed herein can be used to administer biophotons to a subject. In some cases, the administration of biophotons to a subject is referred to herein a biophoton therapy.

Biophoton therapy can be administered to a subject by placing a medical device near the subject. For example, a medical device can be placed under a bed, next to a bed, on a nightstand, on or under a table, under a chair, packed in a backpack, or in any location that is in proximity to the subject.

In some embodiments, to receive biophoton therapy, a subject can be within in a range of about: 0.1 meter to about 20 meters, 0.1 meters to about 1 meter, 0.5 meters to about 3 meters, 0.1 meters to about 10 meters, 0.5 meters to about 10 meters, 1 meter to about 10 meters, 0.5 meter to 5 meters, 2 meters to 8 meters, 5 meters to about 15 meters or about 10 meters to about 20 meters to a medical device. In some cases, to receive biophoton therapy, a subject can be at a distance of more than, less than, or equal to about: 0.1 meters, 0.2 meters, 0.3 meters, 0.4 meters, 0.5 meters, 0.6 meters, 0.7 meters, 0.8 meters, 0.9 meters, 1 meters, 2 meters, 3 meters, 4 meters, 5 meters, 6 meters, 7 meters, 8 meters, 9 meters, 10 meters, 11 meters, 12 meters, 13 meters, 14 meters, 15 meters, 16 meters, 17 meters, 18 meters, 19 meters, or 20 meters to a medical device. In some cases, the biophotons can be active on direct contact with a subject, for example if a subject is touching a medical device.

In some embodiments, a biophoton therapy can be administered as needed, or for: one day, two days, three days, four days, five days, six days, a week, two weeks, three weeks, a month, two months, three months, four months, five months, six months, seven months, eight months, nine months, ten months, eleven months, a year, two years, or chronically.

In some embodiments, a biophoton therapy can be administered continuously or intermittently for a total exposure of about: 5 minutes to about 24 hours, 5 minutes to about 60 minutes, 10 minutes to about 30 minutes, 5 minutes to about 20 minutes, 15 minutes to about 30 minutes, 20 minutes to about 40 minutes, 40 minutes to about 60 minutes, 30 minutes to about 60 minutes, 1 hour to about 1.5 hours, 1 hour to about 2 hours, 2 hours to about 4 hours, 3 hours to about 6 hours, 5 hours to about 10 hours, 7 hours to about 12 hours, 8 hours to about 16 hours, 12 hours to about 24 hours, or about 24 hours to about 48 hours per dose. In some embodiments, a biophoton therapy can be administered continuously or intermittently for a total exposure of more than, less than, or equal to about: 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min per dose. In some embodiments, a biophoton therapy can be administered continuously or intermittently for a total exposure of more than, less than, or equal to about: 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours per dose. In some cases, a biophoton therapy can be administered in about: 1 dose, 2 doses, 3 doses, 4 doses, 5 doses, 6 doses, 7 doses, 8 doses, 9 doses, 10 doses, or more than 10 doses.

In some embodiments, administering of biophoton therapy (e.g., by a medical device) can be performed at least about: 1 time per day, 2 times per day, 3 times per day, 4 times per day, 5 times per day, 6 times per day, 7 times per day, 8 times per day, 9 times per day, or more than 9 times per day. In some cases, administration of a biophoton therapy can be performed at least 1, 2, 3, 4, 5, 6, 7, 8, 9, 10, 11, 12, 13, 14, 15, 16, 17, 18, 19, 20, 21, 22, 23, or 24 times in a 24-hour period. In some cases, administration of a biophoton therapy can be performed at least: 1, 2, 3, 4, 5, 6, 7, 8, 9, 10, 11, 12, 13, 14, 15, 16, 17, 18, 19, 20, or 21 times a week. In some cases, administration of a biophoton therapy can be performed at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, or more than 90 times a month. In some cases, administering can be performed daily, weekly, monthly, or as needed. In some cases, administration can be performed by a subject (e.g., the patient), a health care provider, or both.

In some embodiments, administering of biophoton therapy can be performed for a treatment duration of at least about, or equal to: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, or 1000 days consecutive or nonconsecutive days. In some cases, a treatment duration of a biophoton therapy can be from about 1 to about 30 days, from about 10 to about 30 days, from about 25 to about 60 days, from about 45 to about 90 days, from about 100 to about 300 days, from about 200 to about 500 days, or from about 250 days to about 1000 days.

In some embodiments, administering of biophoton therapy can be performed for a treatment duration of at least about 1 day, at least about 1 week, at least about 1 month, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or for life. Administration can be performed repeatedly over a lifetime of a subject, such as once a day, once a week, once a month or once a year for the lifetime of a subject.

In some embodiments, a biophoton therapy can be administered with 1 or more medical devices. In some cases, a biophoton therapy can be administered with about: 1 medical device to about 100 medical devices, 1 medical device to about 20 medical devices, 1 medical device to about 5 medical devices, 5 medical devices to about 15 medical devices, 1 medical device to about 10 medical devices, 10 medical devices to about 25 medical devices, 20 medical devices to about 50 medical devices, 30 medical devices to about 60 medical devices, 50 medical devices to about 80 medical devices, 60 medical devices to about 90 medical devices, or about 80 medical devices to about 100 medical devices. In some cases, a biophoton therapy can be administered with at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 medical devices.

In some cases, administering a biophoton therapy herein can comprise administering an amount sufficient to treat a disease, condition, and/or symptom. In some cases, administering a biophoton therapy herein can comprise administering a range of about: 1 million to about 40 million biophotons, 1 million to about 10 million biophotons, 5 million to about 15 million biophotons, 10 million to about 20 million biophotons, 15 million to about 25 million biophotons, 20 million to about 30 million biophotons, 25 million to about 35 million biophotons, or about 30 million to about 40 million biophotons in 600 μm$^2$/sec as measured by a MIRA camera. In some cases, administering a biophoton therapy herein can comprise administering more than about, less than about, or equal to about: 1 million biophotons, 2 million biophotons, 3 million biophotons, 4 million biophotons, 5 million biophotons, 6 million biophotons, 7 million biophotons, 8 million biophotons, 9 million biophotons, 10 million biophotons, 11 million biophotons, 12 million biophotons, 13 million biophotons, 14 million biophotons, 15 million biophotons, 16 million biophotons, 17 million biophotons, 18 million biophotons, 19 million biophotons, 20 million biophotons, 21 million biophotons, 22 million biophotons, 23 million biophotons, 24 million biophotons, 25 million biophotons, 26 million biophotons, 27 million biophotons, 28 million biophotons, 29 million biophotons, 30 million biophotons, 31 million biophotons, 32 million biophotons, 33 million biophotons, 34 million biophotons, 35 million biophotons, 36 million biophotons, 37 million biophotons, 38 million biophotons, 39 million biophotons, 40 million biophotons in 600 μm$^2$/sec as measured by a MIRA camera.

In some cases, a biophoton therapy can be administered when the subject is awake, or sleeping. In some cases, a biophoton therapy can be administered when the subject is stationary, for example at work. In some instances, a medical device can be placed under or near the bed of a subject. In some cases, a medical device can be placed at any location that is near the subject, for example on a desk, in backpack of a subject, or under a chair of a subject.

Kits

In some embodiments, a medical device disclosed herein can be comprised in a kit. In some cases, the materials for a medical device (e.g., a stone, a polymer, a metal, a sand, a water and/or an unactivated ingredient) can be comprised in a kit. In some cases, the materials are comprised in a kit individually or in combination. In some cases, a kit can comprise a container. In some cases, a container can be any container such as a glass container, a metal container, a plastic container, a wood container, or any combination thereof.

EXAMPLES

Example 1: Biophoton Release Comparison Between Two Medical Devices

Two medical device devices were tested for their ability to generate biophotons.

The first device (Device A) was an early medical device that comprised: copper powder—100 grams, tourmaline powder—100 grams, sand comprising silicon dioxide—100 grams, water—50 grams, grout—150 grams, for a total weight of 500 grams. The second device (Device B) was an updated device that comprised: fine isoprene rubber powder—250 grams, copper powder—50 grams, tourmaline powder—50 grams, sand comprising silicon dioxide—50 grams, water—50 grams, grout—50 grams, for a total weight of 500 grams. The particle sizes of the copper powder, tourmaline powder, sand, and isoprene rubber were with the range of 0.1 mm to 5 mm in diameter.

Figure 1B:
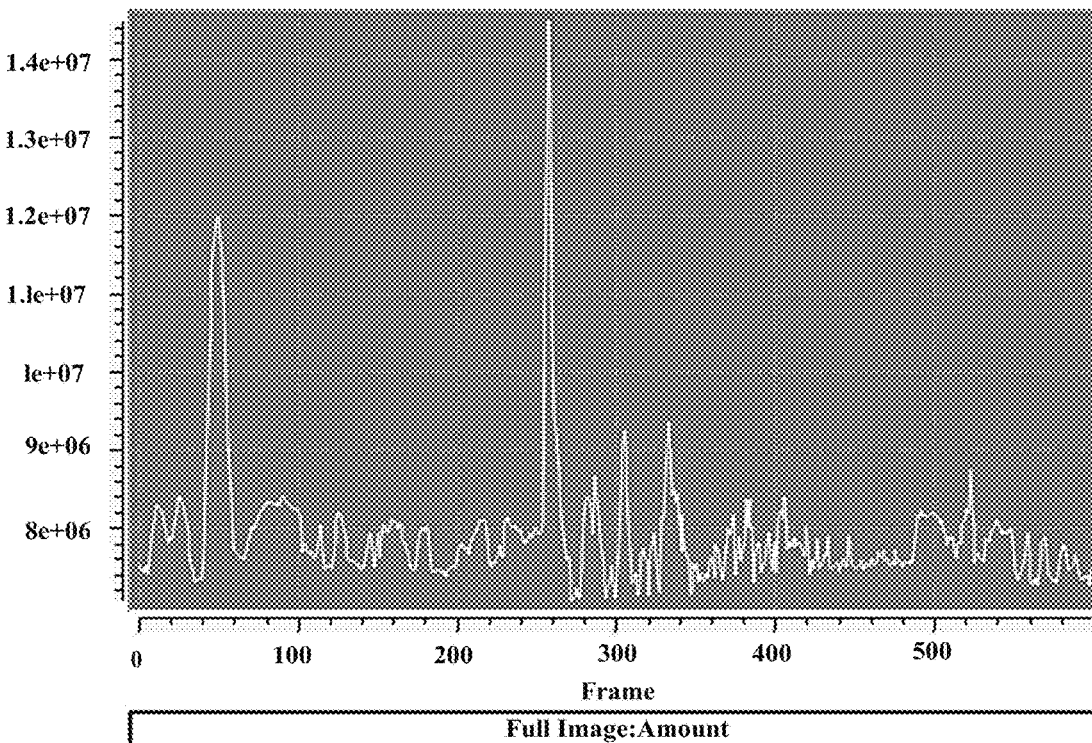

FIG. 1A shows Device A released about 7 million biophotons in 600 μm$^2$/see as measured by a MIRA camera. In comparison, FIG. 1B shows Device B released about 8 million biophotons in 600 μm$^2$/see as measured by a MIRA camera. This data was reproducible in independent replicates. The multispectral video camera counts the number of biophotons per second released from a 600×600 μm window. Overall, for the exemplified experiments there was a total biophoton emission of about 130,000,000 biophotons from Device A and about 140,000,000 biophotons from Device B for the recorded session. The data shows the updated medical device (Device B) with added isoprene rubber powder surprisingly and unexpectedly produced more biophotons than the original medical device.

Example 2: Biophoton Release Comparison Between Combined Materials and a Single Material Two medical device devices were tested for their ability to generate biophotons. The medical devices that were tested were a medical device that comprised a single stone and a medical device that comprised a mix of materials. The medical device that comprised a single stone comprised: tourmaline powder—300 grams, sand comprising silicon dioxide—100 grams, water—50 grams, grout—50 grams, for a total mixture weight of 500 grams. The medical device that comprised a mix of materials comprised: tourmaline powder—200 grams, isoprene rubber powder—100 grams, copper powder—50 grams, sand comprising silicon dioxide 50 grams, water 50 grams, grout 50 grams, total 500 grams. The particle sizes of the copper powder, tourmaline powder, sand, and isoprene rubber were within the range of 0.1 mm to 5 mm in diameter.

Figure 2:
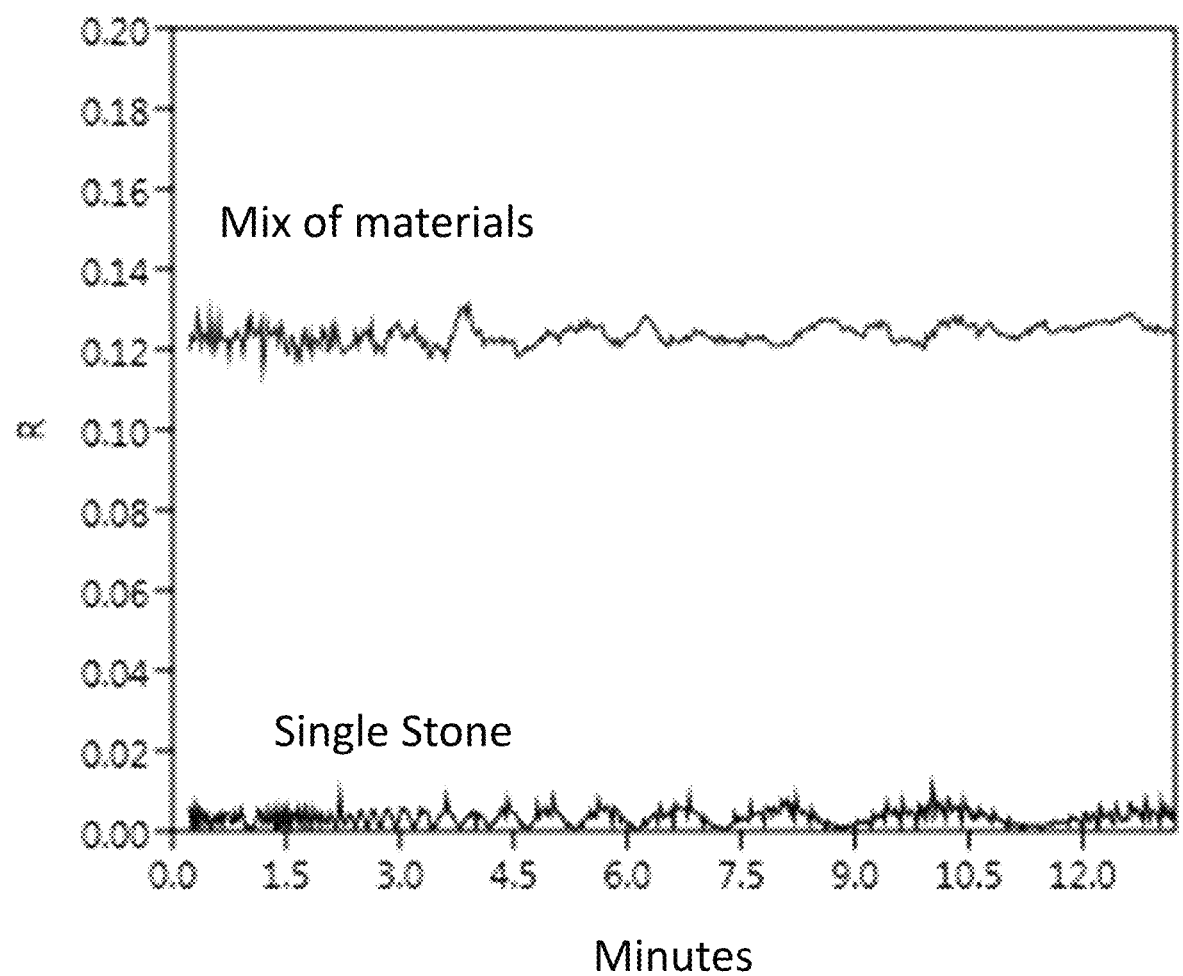
FIG. 2 shows the difference of the biophotons released from a single stone and a finished product (containing a mix of materials) detected by a biophoton detection camera. The Y-axis shows the strength of the biophoton signal. The X-axis shows the time in minutes.

The device that contained a mix of materials produced more biophotons than the device with a single stone as shown in FIG. 2. The device comprising the mix of materials produced 12x more biophotons as compared to the device with a single stone. The biophotons were measured by a single photon detector produced by Thorlabs. The intensity of biophotons over 30 minutes was measured for each product. The measurement was reproducible in independent replicates. The Y-axis indicates the intensity (strength) of the biophoton signal and the X-axis indicates the time in minutes.

Example 3: Biophoton Therapy for the Treatment of Stroke

A randomized double blinded placebo controlled two group comparison clinical study was conducted on chronic stroke patients. Thirty-three patients with chronic stroke between 0.6 years to 24 years since their last stroke were enrolled in the study.

The patient demographic of the stroke study is shown in Table 1.

TABLE 1

Patient demographic for stroke study

|  | Control | Treatment |
|---|---|---|
| Average Age of Study Participant (Year) | 64 | 68 |
| Female | 6 | 7 |
| Male | 9 | 11 |
| Ischemic Stroke | 11 | 18 |
| Hemorrhagic Stroke | 4 | 0 |
| Mean Duration since Last Stroke | 5.72 years | 2.90 years |
| Shortest Duration since Last Stroke | 0.6 years | 0.8 years |
| Longest Duration since Last Stroke | 24 years | 7.4 years |

The treatment comprised administration of biophoton therapy with a medical device. For the treatment group (and control group once switched to treatment after week 2), medical devices were placed under the bed of the patients with chronic stroke. The treated subjects were each exposed to a group of 14 medical devices each weighing 2.5 kg. The medical devices comprised rubber isoprene powder—1250 grams, copper powder—250 grams, tourmaline powder—250 grams, sand comprising silicon dioxide—250 grams, water—250 grams, grout—250 grams for a total weight of 2500 grams. The placebo (control) group were each exposed to a group of 14 placebo devices each weighing 2.5 kg. The placebo device comprised sand comprising silicon dioxide—2000 grams, water—250 grams, grout—250 grams for a total of 2500 grams. The placebo device emitted a much lower amount of biophotons as compared to the treatment medical device. The particle sizes of the copper powder, tourmaline powder, sand, and isoprene rubber powder were within the range of 0.1 mm to 5 mm in diameter.

The patients in the treatment group were exposed to the devices at a distance of about 40 centimeters for a time ranging from a minimum 8 hours to a maximum of 24 hours per day. The patients in the control group were exposed to the placebo devices at a distance of about 40 centimeters for a time ranging from a minimum of 8 hours to a maximum of 24 hours per day.

The active devices were used for the entire 4 weeks for these patients in the Treatment group. Therefore, these patients were also actively treated for 4 weeks. The placebo devices were used for the first two weeks of the study but were switched to the active biophoton therapy after the first two weeks of placebo treatment. Therefore, these patients were also actively treated for 4 weeks, to be ethically justified.

A variety of metrics were used to compare the treatment group vs. the control group and are described below.

Figure 3:
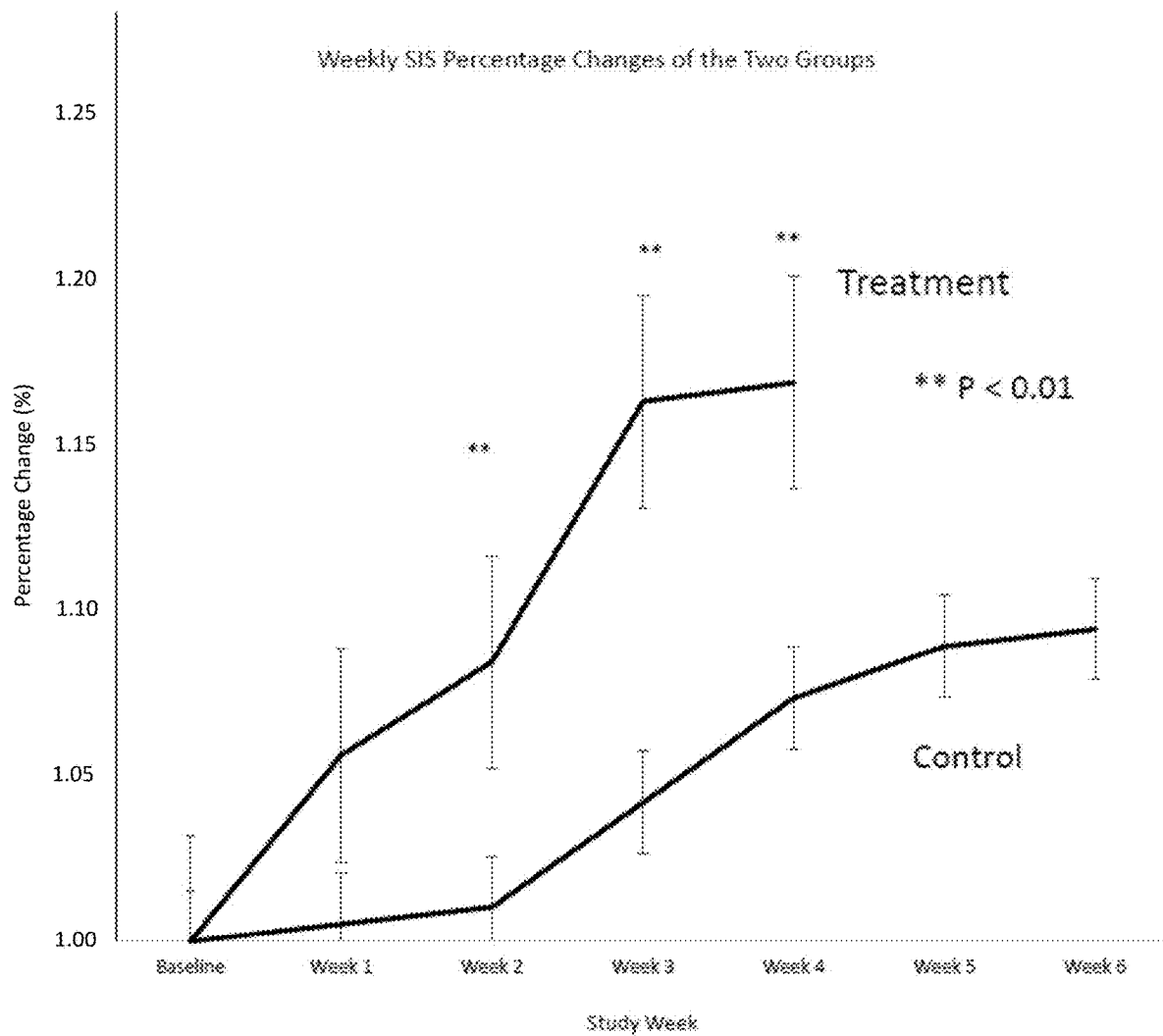
FIG. 3 shows the Stroke Impact Scale (SIS) results of patients with stroke during a randomized double blinded and placebo controlled clinical study. The Y-axis of the figure indicates the SIS score percentage change, the X-axis shows the length of time of the study.

The Stroke Impact Scale (SIS) of the patients in the treatment group increased significantly as compared to the control group (see FIG. 3). The SIS is an internationally used standard research tool to monitor the disease and function status of stroke. The SIS has multiple components. For the current study, scores of SIS were obtained weekly by the clinical study team staffer, from the study participant or his/her caregiver. In FIG. 3 The Y-Axis shows the percentages of the increased SIS as compared to the baseline, the X-axis shows the length of time of the study. The scores for the treatment group were: 1.0 at week 0 (baseline), 1.06 in week 1, 1.08 in week 2, 1.16 in week 3, and 1.17 in week 4. The scores for the control group were: 1.0 at week 0 (baseline), 1.01 in week 1, 1.01 in week 2, 1.04 in week 3, 1.07 in week 4, 1.09 in week 5, and 1.09 in week 6.

Statistical analysis for data in FIG. 3, was completed with a two-group ANOVA analysis and/or a self-comparison against the baseline values, by an ANOVA analysis.

The control group compared to the baseline control group:

Comparing the changes from the baseline at each week (weeks 1 to 6), the p-values are 0.7758 and 0.7328 at Week 1 and 2 before switching to the treatment. After switching to the treatment, the p-values are 0.1137, 0.0332, 0.0019, and 0.0079 after being treated for 1 to 4 weeks respectively. The p-value becomes significant after the treatment was started for 2 weeks. It shows that there was no improvement while patients were on the placebo treatment. The numerical improvement shows immediately after the switch and the improvement becomes significant after the subjects were treated for 2 weeks.

The treatment group compared to the baseline treatment group:

Comparing the changes from the baseline, the p-values are 0.0032, 0.0006, 0.0001, 0.0002 after the treatment started for 1-4 weeks respectively.

Comparing the treatment group against the control group (Comparing the weekly changes from baseline between the two groups):

The p-values are 0.0084, 0.0112, 0.0406, 0.0812. These p-values are for comparing a) 1 week of treatment vs 1 week of placebo; b) 2 weeks of treatment vs 2 weeks of placebo; c) 3 weeks of treatment vs 2 weeks of placebo+1 week of treatment; d) 4 weeks of treatment vs 2 weeks of placebo+2 weeks of treatment, respectively. The change from baseline was statistically significantly between the placebo and the treatment. Although the difference (treated for 3 weeks vs treated for 1 week) was still significant at Week 3, the control group demonstrates numerical improvement. At Week 4, the treatment group still showed improvement compared to the Control, but the difference was no longer significant.

Comparing the two groups after receiving the active treatment for 1-4 weeks. a) treatment Week 1 vs. Control Week 3; b) treatment Week 2 vs. Control Week 4; c) treatment Week 3 vs. Control Week 5; d) treatment Week 4 vs. Control Week 6. The p-values are 0.5059, 0.6215, 0.2570, 0.1443 respectively. After receiving the treatment, there was no difference between these two groups.

Figure 4:
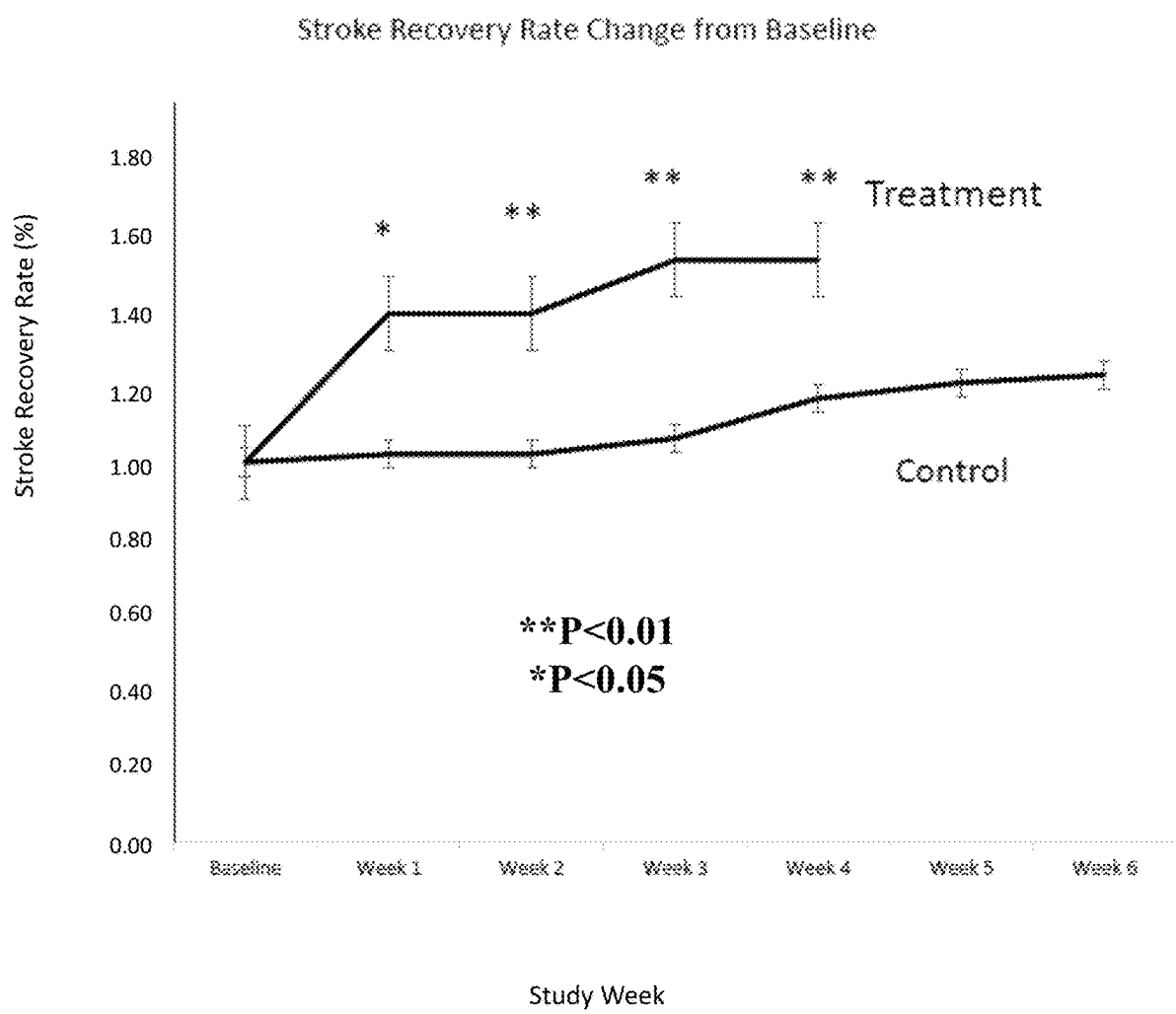
FIG. 4 shows the recovery rates of the patients with stroke during a randomized double blinded and placebo controlled clinical study. The Y-axis of the figure indicates the stroke recovery rate score change as compared to baseline score, the X-axis shows the length of time of the study.

The stroke recovery rate improved in the treatment group after using a medical device. Improvement was seen in the first week of the treatment group (score of 1.39) as compared to the control group (score of 1.02) as shown in FIG. 4. The stroke recovery rate was reported by the study participant or caregiver and verified by the study physician. The stroke recovery rate is an individual measurement on the Stroke Impact Scale (SIS) questionnaire. This increase was maintained throughout the length of the study. Once the control group was switched to the biophoton therapy, there was an increase in stroke recovery rate from week 3 to week 6. In FIG. 4 the Y-Axis shows the percentage of the stroke recovery rate, and the X-axis shows the length of time of the study.

Statistical analysis of the stroke recovery rates between the two groups was completed with a Self-comparison ANOVA against Baseline value and/or a two-group ANOVA analysis:

The Control Group:

Comparing the changes from the baseline at each week (weeks 1 to 6), the p-values are 0.6878 and 0.5232 at Week 1 & 2 before switching to the treatment. After switching to the treatment, the p-values are 0.4560, 0.0003, 0.0005, and 0.0003 after being treated for 1 to 4 weeks respectively. The p-value became significant after the treatment started for 2 weeks. The data shows that there is no improvement while patients were on the placebo treatment. Though it is not significant with a p value of 0.4560 at Week 3 (1 week after switching to the active treatment), there was a numerical improvement. The improvement becomes significant 2 weeks after switching from the placebo to the treatment.

The Treatment Group:

Comparing the changes from the baseline, the p-values are 0.0119, 0.0032, 0.0077, 0.0005 after the treatment started for 1-4 weeks respectively, which shows a statistically significant increase in each week. This is similar with what was observed in the Control group—a numerical improvement was shown after 1 week of treatment and the improvement became statistically significant starting at week 2 of treatment.

Comparing the Treatment Group Against the Control Group: Comparing the Weekly Changes from Baseline Between the Two Groups The p-values are 0.0624, 0.0216, 0.0640, 0.0355. These p-values are for comparing a) 1 week of treatment vs 1 week of placebo; b) 2 weeks of treatment vs 2 weeks of placebo; c) 3 weeks of treatment vs 2 weeks of placebo+1 week of treatment; d) 4 weeks of treatment vs 2 weeks of placebo+2 weeks of treatment. The change from baseline was statistically significantly different between the placebo and the treatment. Although the difference (treated for 3 weeks vs treated for 1 week) was still significant at Week 3, the control group demonstrated numerical improvement. At Week 4, the treatment group showed better improvement comparing to the Control, but the difference was no longer significant.

Comparing the two groups after receiving the active treatment for 1-4 weeks. a) treatment Week 1 vs. Control Week 3; b) treatment Week 2 vs. Control Week 4; c) treatment Week 3 vs. Control Week 5; d) treatment Week 4 vs. Control Week 6. The p-values are 0.5059, 0.6215, 0.2570, 0.1443 respectively. Comparing the improvement after receiving the same time of treatment, there was no difference between these two groups.

Figure 5:
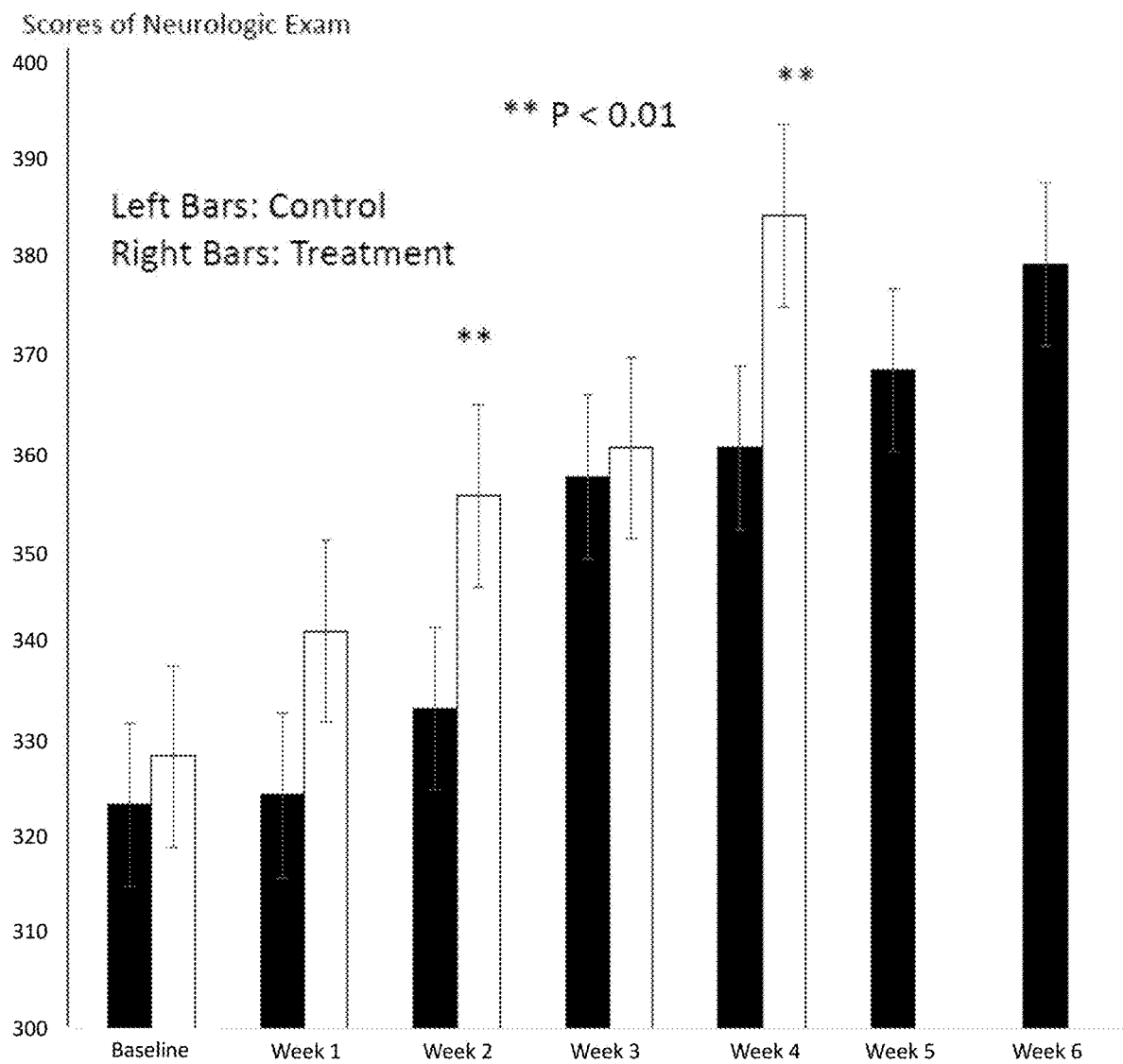
FIG. 5 shows the neurologic examination score of the patients with stroke during a randomized double blinded and placebo controlled clinical study. The Y-axis of the figure indicates the neurological exam score, the X-axis shows the length of time of the study. The black bars are the control patient group, the white bars are the treatment patient group.

The Neurologic Exam Scores of the patients with chronic stroke improved after using medical devices as shown in FIG. 5. The observation of change was performed objectively by the clinical research physician. The neurological exam comprised measuring multiple factors and the total score was summarized by the study physician. The results are shown in FIG. 5. The Y-Axis shows the neurologic exam scores, the X-axis shows the length of time of the study. The scores for the treatment group were: 328 at week 0 (baseline), 341 in week 1, 355 in week 2, 360 in week 3, and 384 in week 4. The scores for the control group were: 323 at week 0 (baseline), 324 in week 1, 333 in week 2, 357 in week 3, 360 in week 4, 368 in week 5, 379 in week 6. The Neurologic Exam Score improved in the treatment group after using a medical device throughout the 4 weeks of the study. Similarly, improvement was seen in the first week of the treatment group (score of 341—change of 13 points from the baseline) as compared to the control group (score of 324—change of 1 point from baseline) as shown in FIG. 5. This increase was maintained throughout the length of the study. Once the control group was switched to the biophoton therapy, there was an increase in Neurologic Exam Scores from week 3 to week 6.

Figure 6:
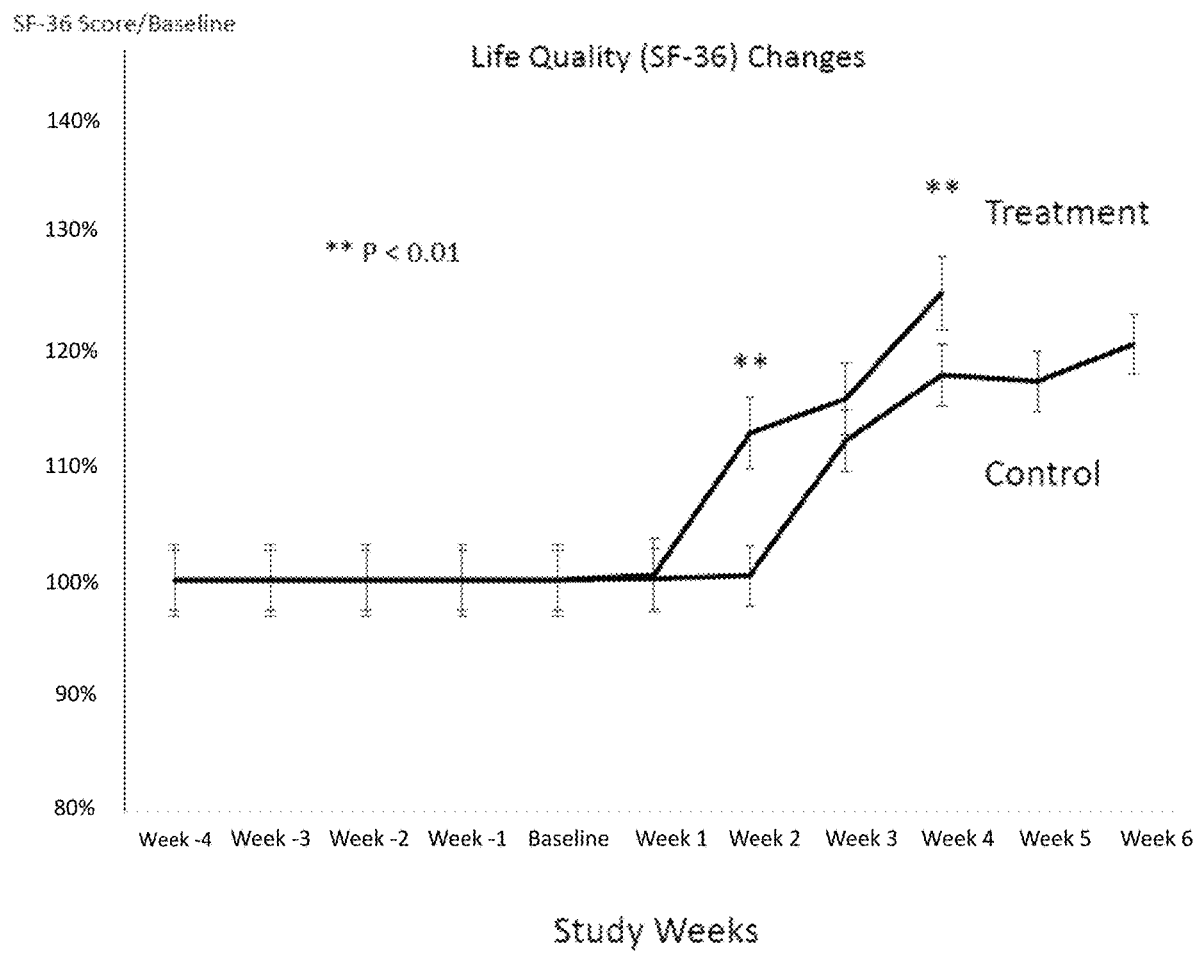
FIG. 6 shows the Life Quality (SF-36 Score) change of the patients with stroke during a randomized double blinded and placebo controlled clinical study. The Y-axis of the figure indicates the SF-36 score change (compared to 100% baseline score), the X-axis shows the length of time of the study.

The life quality of the patients with chronic stroke improved significantly after using medical devices as shown in FIG. 6. To assess the life quality of the patients a SF-36 was administered to the patients in both groups before and during the clinical study. The SF-36 assessment is an internationally used standard research tool to monitor the life quality for many chronic conditions. The total score of the 36 questions was used to calculate the overall SF-36 score. In FIG. 6 The Y-Axis shows the percentage of the SF-36 score as compared to the baseline, the X-axis shows the length of time of the study. As shown in FIG. 6, patients in both the Control and Treatment groups did not have any change 4 weeks before participating in the living-in at-center study. Once exposed to the medical device, the treatment group had an immediate increase in the score. The patients in the placebo-control group did not make any meaningful improvement during the first 2 weeks (the placebo phase) as noted by the constant score. After the control group was switched to the treatment (after week 2), their life quality improved.

As shown in FIG. 6, patients with chronic stroke had no placebo effect for their disability or life quality during the 4 weeks at home before the study, nor 2-week stay in a hotel where the clinical study was conducted. After switching to treatment, they had reduced disability after using the medical device.

In summary, the control group during the first two weeks (placebo phase) did not have any significant changes in SIS percentage change (see FIG. 3), stroke recover rate change (see FIG. 4), neurological exam scores (see FIG. 5), and SF-36 scores (see FIG. 6) as compared to the treatment group which had improvement in all measured assays. After the control group switched to the treatment for 4 weeks, they had improvements in the SIS percentage change, stroke recover rate change, neurological exam scores, and SF-36 scores, which was similar to the treatment group.

Example 4: Biophoton Therapy for the Treatment of Traumatic Brain Injury (TBI)

A randomized double blinded placebo controlled two group comparison clinical study for the treatment of Traumatic Brain Injury (TBI) is ongoing. The study comprises thirty-two patients with Traumatic Brain Injury.

The treatment comprises administration of biophoton therapy with a medical device. The treatment group (and control group once switched to treatment after week 2) are exposed to a group of 14 medical devices that each weigh 2.5 kg. The medical devices comprise isoprene rubber powder—1250 grams, copper powder—250 grams, tourmaline powder—250 grams, sand comprising silicon dioxide—250 grams, water—250 grams, grout—250 grams, for a total of 2500 grams. The control subjects are exposed to a group of 14 placebo devices that each weigh 2.5 kg. The placebo devices comprise sand comprising silicon dioxide—2000 grams, water—250 grams, grout—250 grams, for a total weight of 2500 grams. The placebo device emitted a much lower amount of biophotons as compared to the treatment medical device. The particle sizes of the copper powder, tourmaline powder, sand, and isoprene rubber powder were within the range of 0.1 mm to 5 mm in diameter.

The patients in the treatment group are each exposed to 14 devices at a distance of about 40 centimeters for a time ranging from a minimum 8 hours to a maximum of 24 hours per day. The patients in the control group are each exposed to the 14 placebo devices at a distance of about 40 centimeters for a time ranging from a minimum of 8 hours to a maximum of 24 hours per day. The active medical devices are used for the entire 4 weeks for the patients in the treatment group. For the control group, the placebo devices are used for the first two weeks of the study but are switched to active medical devices after the first two weeks of placebo treatment. Therefore, these patients are also actively treated for 4 weeks, to be ethically justified.

Preliminary results showed no change in the placebo group during the first two-weeks of the trial in disability, functionality, and a physician-conducted neurologic examination. After switching to the treatment for 4 weeks, the placebo group showed improvements in the physician-conducted neurologic examination, improvements in pain, and improvements in SF-36 scores which were similar to the treatment group.

Example 5: Biophoton Therapy for the Treatment of Alzheimer's Disease

A randomized triple blinded placebo controlled clinical study was conducted to verify if biophotons can improve cognition of patients with Alzheimer's disease. The clinical trial enrolled a total of 30 participants diagnosed with moderate to severe AD. All participants continued their standard care if any. During a 4-week observational period, 16 participants in the treatment group individually used a group of 14 medical devices daily. The medical devices each weighted 2.5 kg and comprised isoprene rubber powder—1250 grams, copper powder—250 grams, tourmaline powder—250 grams, sand comprising silicon dioxide—250 grams, water—250 grams, grout—250 grams, for a total weight of 2500 grams. The placebo device emitted a much lower amount of biophotons as compared to the treatment medical device. The particle sizes of the copper powder, tourmaline powder, sand, and isoprene rubber powder were within the range of 0.1 mm to 5 mm in diameter.

Preliminary outcome: cognitive function was assessed by using an Alzheimer Questionnaire, life quality was measured using a SF-36 life quality questionnaire; and electroencephalogram (EEG) measurements were assessed using standardized measurements. Preliminary analysis reveals an improvement in cognitive performance among participants in the biophoton therapy group compared to the control group. Seventy-five percent (75%) of participants had reduced severity of Alzheimer's disease; and 88% had an increased life quality SF-36 score. All were significantly different from the Control group (P<0.01)—statistics were completed with a self-comparison ANOVA. The EEG test also showed that the "missed response" was reduced in the Treatment group. In addition, caregivers reduced the stress and difficulty in caring for their seniors. No adverse effects were observed.

Example 6: Biophoton Energized Water

Figure 7:
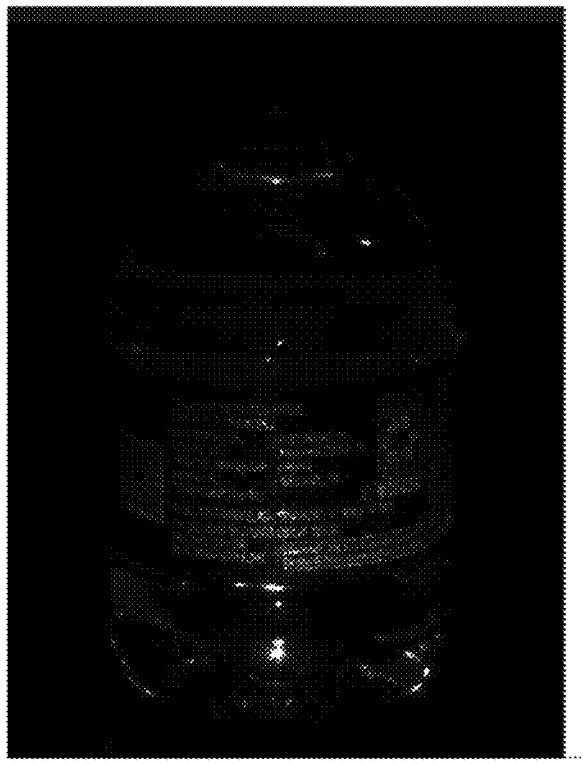
FIG. 7 shows the difference readings of biophotons of a water bottle before and after being energized with a strong medical device.
Figure 7:
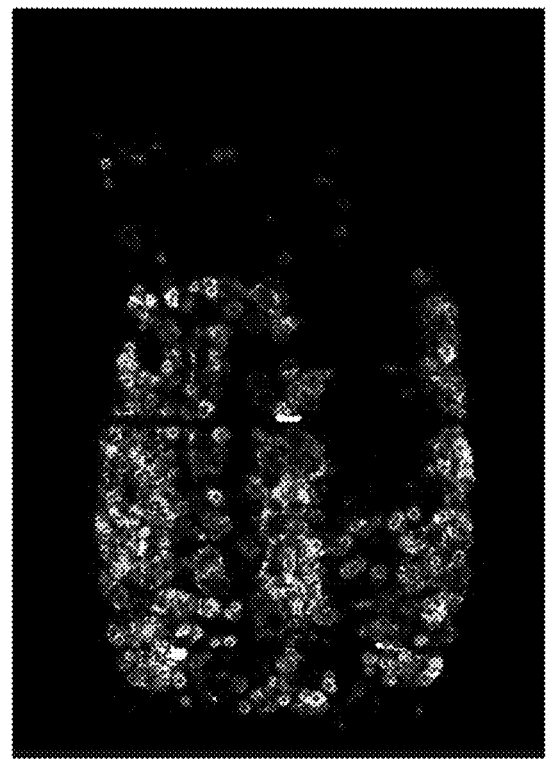

FIG. 7 shows an image of the biophotons of a water bottle before and after being energized with a strong medical device. A bottle of water was exposed for over 24 hours to 4 medical devices each weighing 45 kg. The medical devices comprised isoprene rubber—22,500 grams, copper powder—4500 grams, tourmaline powder—4500 grams, sand—4500 grams, water—4500 grams, grout—4500 grams, for a total weight of 45,000 grams. The particle sizes of the copper powder, tourmaline powder, sand, and isoprene rubber powder were within the range of 0.1 mm to 5 mm in diameter. An image of the energized water is shown in FIG. 7. The image was captured using a MIRA camera.

Example 7: Biophoton Energy Generator

A medical device was made by contacting isoprene rubber—22,500 grams, copper powder—4500 grams, tourmaline powder—4500 grams, sand comprising silicon dioxide—4500 grams, water—4500 grams, grout—4500 grams, for a total weight of 45,000 grams and mixed into a heterogeneous mixture. The composition was allowed to solidify and sealed into a container. The particle sizes of the copper powder, tourmaline powder, sand, and isoprene rubber powder were within the range of 0.1 mm to 5 mm in diameter.

Example 8: Treatment of Disease with a Medical Device

A patent suffering from any disease or condition enumerated herein is administered a biophoton therapy with one or more medical devices. The biophoton therapy is administered for at least: 6, 7, or 8 hours a day for about 1, 2, 3, or 4 weeks. The biophoton therapy is administered to a patient that is within 0.1 meters to 3 meters from the one or more medical devices. After biophoton therapy for about 1, 2, 3, or 4 weeks the patient demonstrates an improvement in their disease which can be a quantifiable improvement.

While preferred embodiments of the present disclosure have been shown and described herein, it will be obvious to those skilled in the art that such embodiments are provided by way of example only. Numerous variations, changes, and substitutions can occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating a stroke in a subject in need thereof, the method comprising placing a medical device within about 0.1 meters to about 5 meters from a subject for at least about 1 hour per day, wherein the medical device comprises a substantially heterogeneous mixture of:
   (a) a stone selected from the group consisting of: a diamond, an amethyst, a tourmaline, a jade, an obsidian, and any combination thereof;
   (b) a sand comprising at least about 95% silicon dioxide by weight;
   (c) a metal selected from the group consisting of: a copper, an iron, and any combination thereof;
   (d) a polymer selected from the group consisting of: an isoprene rubber, a butyl rubber, a cellulose, a polysaccharide, or any combination thereof;

(e) a water; and (d) a supporting material selected from the group consisting of: a grout, a modified sulfur cement, an agar, and any combination thereof;

wherein the stone, the sand, the metal, and the polymer comprise particles that each comprise a particle size diameter ranging from about 0.1 mm to about 5 mm; wherein the medical device comprises biophotons as measured by a biophoton detector and thereby treating the stroke in the subject in need thereof.

2. The method of claim 1, wherein the supporting material is the grout.

3. The method of claim 1, wherein the weight to weight ratio of the stone, the sand, the metal, the polymer, the water and the supporting material is about 10% the stone: 10% the sand: 10% the metal: 50% the polymer: 10% the water: and about 10% the supporting material.

4. The method of claim 1, wherein the stone is the diamond.

5. The method of claim 1, wherein the stone is the amethyst.

6. The method of claim 1, wherein the stone is the tourmaline.

7. The method of claim 1, wherein the stone is the jade.

8. The method of claim 1, wherein the stone is the obsidian.

9. The method of claim 1, wherein the metal is the copper.

10. The method of claim 1, wherein the metal is the iron.

11. The method of claim 1, wherein the polymer is the isoprene rubber.

12. The method of claim 1, wherein the polymer is the butyl rubber.

13. The method of claim 1, wherein the polymer is the cellulose and comprises an alpha cellulose or a salt thereof.

14. The method of claim 1, wherein the polymer is the polysaccharide and comprises a hyaluronic acid or a salt thereof.

15. The method of claim 1, wherein the supporting material is the modified sulfur cement.

16. The method of claim 1, wherein the medical device is placed within about 0.1 meters to about 5 meters from the subject for at least about 8 hours per day for at least 1 week.

17. The method of claim 1, wherein the subject in need thereof has an increase in their Stroke Impact Scale (SIS) score after about 1 week of treatment as compared to a subject who was not within about 0.1 meters to about 5 meters from the medical device for at least about 1 hour per day.

18. The method of claim 1, wherein the subject in need thereof has an increase in their SF-36 score after about 1 week of treatment as compared to a subject who was not within about 0.1 meters to about 5 meters from the medical device for at least about 1 hour per day.

19. The method of claim 1, wherein the subject in need thereof has an increase in their stroke recovery rate score after about 1 week of treatment as compared to a subject who was not within about 0.1 meters to about 5 meters from the medical device for at least about 1 hour per day.

20. The method of claim 1, wherein the substantially heterogeneous mixture is a solid mixture.

\* \* \* \* \*